US010876145B2

(12) United States Patent
Ensor et al.

(10) Patent No.: US 10,876,145 B2
(45) Date of Patent: Dec. 29, 2020

(54) FIBER SAMPLER FOR RECOVERY OF BIOAEROSOLS AND PARTICLES

(71) Applicant: Research Triangle Institute, Research Triangle Park, NC (US)

(72) Inventors: David S. Ensor, Chapel Hill, NC (US); Howard Jerome Walls, Apex, NC (US); Karin K. Foarde, Chapel Hill, NC (US); Susanne Vera Hering, Berkeley, CA (US); Steven Russel Spielman, Berkeley, CA (US)

(*) Notice: Subject to any disclaimer, the term of this patent is extended or adjusted under 35 U.S.C. 154(b) by 0 days.

(21) Appl. No.: 16/884,764

(22) Filed: May 27, 2020

(65) Prior Publication Data

US 2020/0347434 A1    Nov. 5, 2020

Related U.S. Application Data

(60) Continuation of application No. 16/455,067, filed on Jun. 27, 2019, now Pat. No. 10,767,210, which is a division of application No. 14/378,768, filed as application No. PCT/US2013/026683 on Feb. 19, 2013, now Pat. No. 10,378,042.

(60) Provisional application No. 61/600,366, filed on Feb. 17, 2012.

(51) Int. Cl.
 *C12Q 1/24*          (2006.01)
(52) U.S. Cl.
 CPC ................................. *C12Q 1/24* (2013.01)
(58) Field of Classification Search
 CPC ..................................................... C12Q 1/24
 See application file for complete search history.

(56) References Cited

U.S. PATENT DOCUMENTS

| 3,926,561 | A |   | 12/1975 | Lucero |
| 4,921,642 | A | * | 5/1990  | LaTorraca ......... A61M 16/1075 128/203.27 |
| 5,738,808 | A | * | 4/1998  | Iwamoto ............... A61M 16/16 128/204.13 |

(Continued)

FOREIGN PATENT DOCUMENTS

WO      2009140385 A1   11/2009

OTHER PUBLICATIONS

European Extended Search Report issued in counterpart EP Application No. 11818728.5 dated Dec. 8, 2017 (twelve (12) pages).

(Continued)

*Primary Examiner* — Nathaniel T Woodward
(74) *Attorney, Agent, or Firm* — Olive Law Group PLLC; Ronald A. Rudder

(57) ABSTRACT

An aerosol collection system and method. The system includes a bio-aerosol delivery device configured to supply bioparticles in a gas stream, a moisture exchange device including a partition member coupled to the gas stream and configured to humidify or dehumidify the bioparticles in the gas stream, and an aerosol collection medium downstream from the moisture exchange device and configured to collect the bioparticles. The method includes delivering bioparticles in a gas stream, humidifying or dehumidifying the bioparticles in the gas stream by transport of water across a partition member and into a vapor phase of the gas stream, and collecting the bioparticles by a collection medium.

20 Claims, 41 Drawing Sheets

(56) References Cited

U.S. PATENT DOCUMENTS

| | | | | |
|---|---|---|---|---|
| 5,996,976 | A * | 12/1999 | Murphy | H01M 8/04119 261/104 |
| 6,269,679 | B1 * | 8/2001 | McCarthy | G01N 13/00 600/323 |
| 6,363,930 | B1 * | 4/2002 | Clawson | A61M 16/1045 128/201.13 |
| 6,669,177 | B2 * | 12/2003 | Shimanuki | B01D 63/02 261/104 |
| 6,864,005 | B2 * | 3/2005 | Mossman | H01M 8/04119 429/414 |
| 7,926,368 | B2 | 4/2011 | Ryan | |
| 2005/0045032 | A1 | 3/2005 | Dasgupta et al. | |
| 2005/0244980 | A1 * | 11/2005 | Hering | G01N 30/12 436/161 |
| 2005/0247619 | A1 * | 11/2005 | Berger | H01M 8/04141 210/321.89 |
| 2005/0248045 | A1 * | 11/2005 | Anthony | A61M 16/16 261/154 |
| 2006/0021615 | A1 * | 2/2006 | Kertzman | A61M 16/1045 128/201.13 |
| 2008/0110342 | A1 | 5/2008 | Ensor et al. | |
| 2008/0233636 | A1 | 9/2008 | Ryan | |
| 2009/0026130 | A1 | 1/2009 | Chikura et al. | |
| 2009/0061496 | A1 | 3/2009 | Kuhn et al. | |
| 2010/0031617 | A1 | 2/2010 | Ensor et al. | |
| 2010/0162473 | A1 | 7/2010 | Willis et al. | |
| 2010/0186524 | A1 | 7/2010 | Ariessohn et al. | |
| 2010/0242633 | A1 | 9/2010 | McDevitt et al. | |
| 2011/0111387 | A1 * | 5/2011 | Wu | G01N 15/06 435/5 |
| 2012/0297979 | A1 * | 11/2012 | Klingenburg | F24F 3/14 95/213 |

OTHER PUBLICATIONS

International Search Report issued in counterpart PCT Application No. PCT/US2013/026683 dated Jul. 9, 2013.

* cited by examiner

Figure 1

| Category | Example Organisms/Toxins | Sampling Challenges |
|---|---|---|
| DNA viruses | Pox viruses | Enveloped viruses, need to maintain at RH <70% |
| RNA viruses | Filoviruses: Arenaviruses, *Alphavirus* | |
| Gram-positive bacteria | *Bacillus anthracis* | Spore-former, most resistant to desiccation; need to ensure that there is not enough water for the spore to germinate |
| Gram-negative bacteria | *Brucella* species, *Burkholderia mallei*, *Yersinia pestis*, *Coxiella burnetii* | Susceptible to desiccation; some may be susceptible to oxygen toxicity; therefore, need to maintain at <70% RH, but not allow desiccation |
| Gram-variable bacteria | *Francisella tularensis* | Susceptible to desiccation, but not to oxygen toxicity; stain Gram-variable, but has Gram-negative cell wall |
| Intracellular bacteria | *Chlamydophila psittaci* (formerly *Chlamydia psittaci*), *Rickettsia prowazekii* | *C. psittaci* forms elementary bodies that are somewhat resistant to environmental stressors |
| Toxins | *Staphylococcus* enterotoxin B, Ricin toxin, *Clostridium botulinum* toxin, epsilon toxin of *Clostridium perfringens* | No viability issues with toxins because they are molecules; however, inactivation of the toxins may occur |

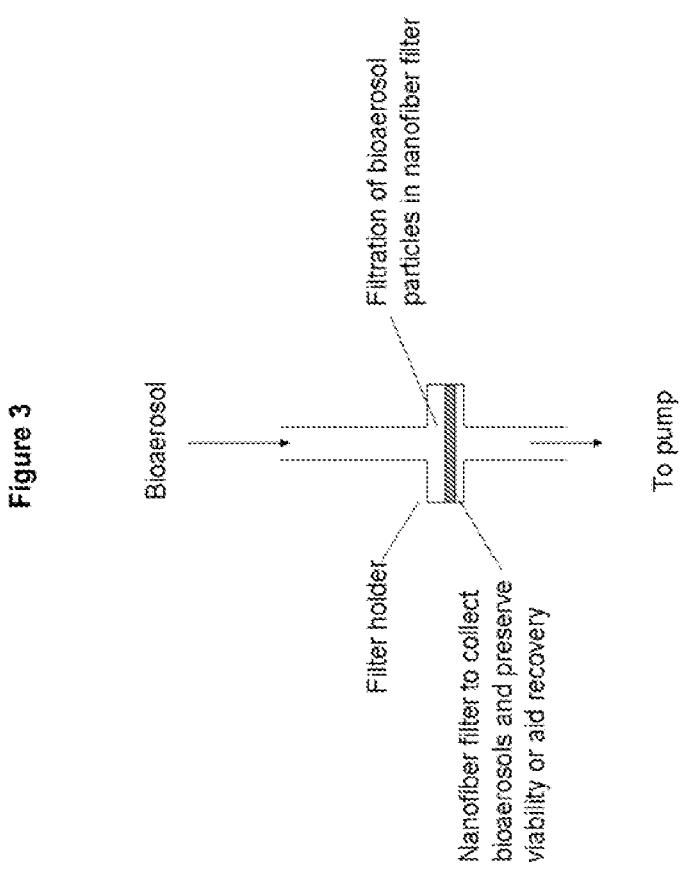

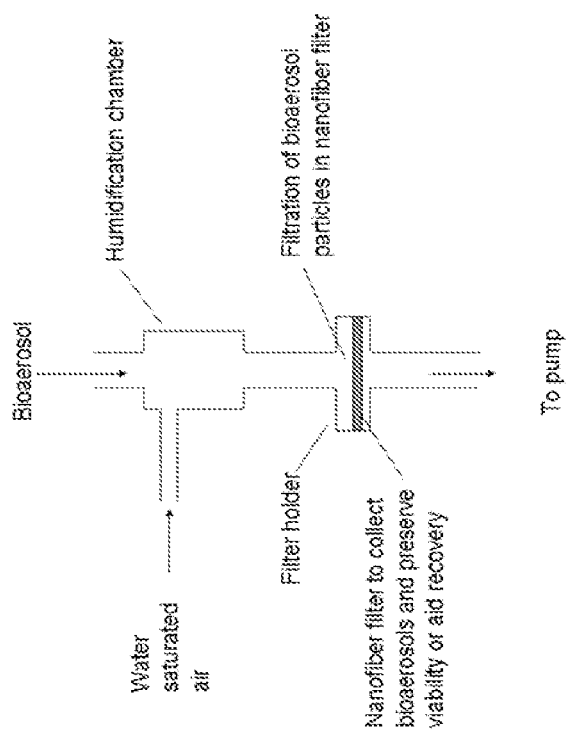

Figure 9

Table 1.

| Polymers | Surface Chemistry |
|---|---|
| Polysulfone (PSU) chemistries | Hydrophobic, Aromatic |
| Nylon chemistries | Hydrophilic, amine like |
| Polyurethane (PU) chemistries | Varies |
| PU absorbent | Hydrophilic |
| PU water resistance | Hydrophobic |
| PU blend formulations | Varies |
| Polycaprolactone (PCL) | Hydrophilic, alkane w/ carbonyl |
| Polystyrene (PS) | Hydrophobic, PE w/ aromatic side chain |
| Gelatine | Hydrophilic, derivative of collagen |

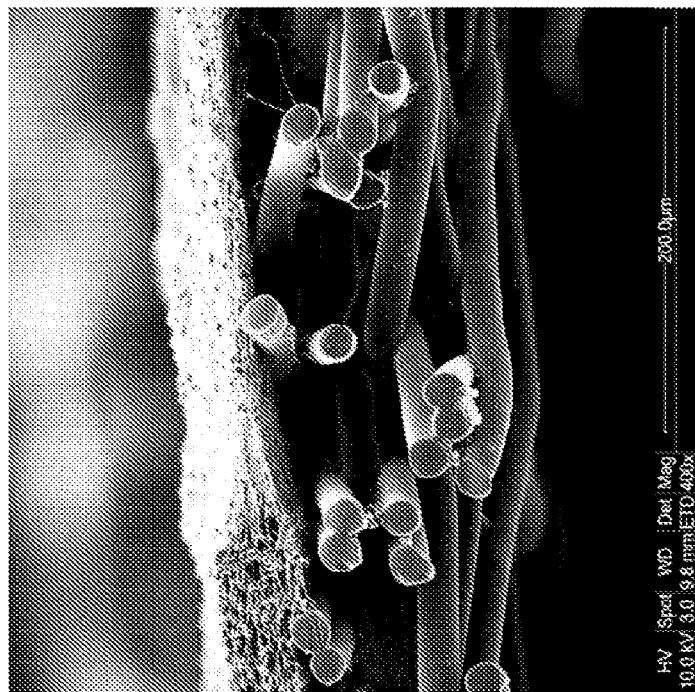

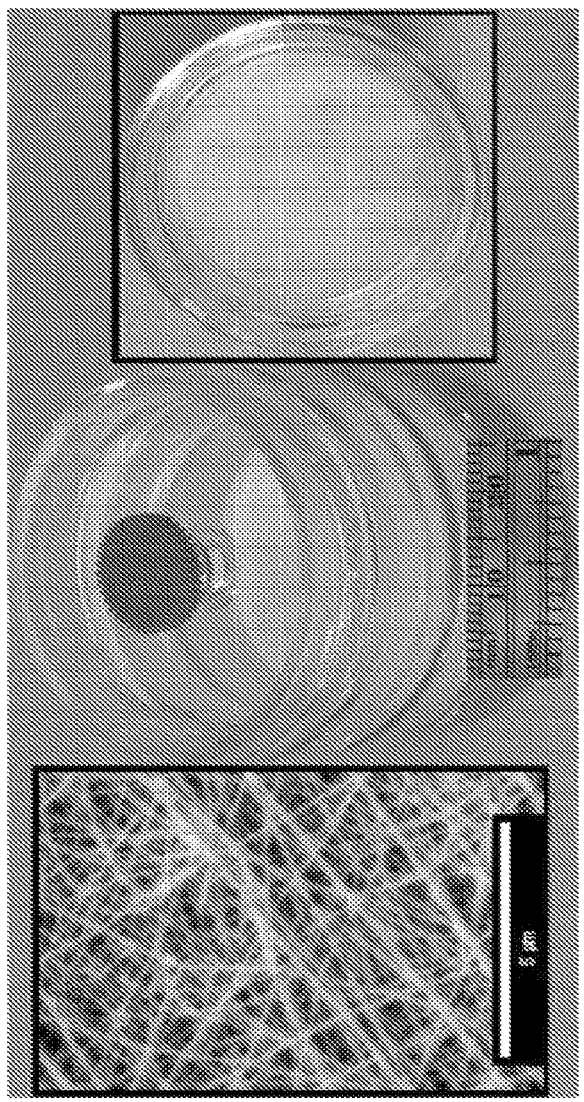

Figure 13

Table 2

| Statistics | Filter Material | Culturable PFU/L air | Collection Efficiency Relative to AGI | % Viable | % Viability[a] Collection Efficiency |
|---|---|---|---|---|---|
| | Teflon[a] | 1.1E+02 | 37% | 6% | 22% |
| Mean ±CV | Polysulfone nanofiber | 1.9E+02 ±0.47 | 88% | 8% | 70% |
| Mean ±CV | Polystyrene nanofiber | 1.0E+02 ±0.16 | 39% | 4% | 16% |

Figure 14

*Serratia*

| Sample Duration | Material | % AGI |
|---|---|---|
| 3 hr | PSU nanofibers | 1% |
| 3 hr | PU nanofibers | 3% |
| 3 hr | SKC Gelatin | 3% |
| 3 hr | Teflon | 0.5% |

Figure 15

*Serratia*

| Face Velocity (cm/min) | PU nanofibers | Gelatin |
|---|---|---|
| 1,020 | 7% | 3% |
| 2,040 | 9% | 14% |
| 4,070 | 10% | ruptured |
| 5,090 | 18% | |

Figure 17A

Table 3

| Material | Lightly protected organism | | | | | |
|---|---|---|---|---|---|---|
| | *Erwinia* | | *P. fluorescens* | | MS2 phage | |
| | 30% RH | 75% RH | 30% RH | 75% RH | 30% RH | 75% RH |
| Nanofiber substrates | | | | | | |
| PSu on non-adsorbent backing | Alive D6 | Dead | Alive D3 | Dead | Alive D7 | Alive D7 |
| PSu on adsorbent paper backing | Dead | Alive D3 | Dead | Alive D4 | Alive D7 | Alive D7 |
| Nylon 6 | Dead | Dead | Dead | Dead | Alive D4 | Alive D7 |
| Polyurethane | Alive D5 | Dead | Alive D3 | Alive D5 | Alive D7 | Alive D7 |
| Other materials | | | | | | |
| Polyurethane foam | Alive D4 | Alive D3 | Alive D4 | Alive D4 | *No data* | Alive D7 |
| Teflo | Alive D5 | Alive D5 | Dead | *No data* | Alive D7 | Alive D7 |
| Gelatin | Alive D5 | Alive D7 | Dead | Alive D7 | Alive D7 | Alive D7 |

Figure 17B

Table 4

| Material | Erwinia | | Well protected organism | | | | S. epidermidis | |
|---|---|---|---|---|---|---|---|---|
| | | | | | P. fluorescens | | | |
| | 30% RH | 75% RH | 30% RH | 75% RH | 30% RH | 75% RH | 30% RH | 75% RH |
| Nanofiber substrates | | | | | | | | |
| PSu on non-adsorbent backing | Dead | Dead | | | Dead | Dead | Alive D4 | Alive D4 |
| PSu on adsorbent paper backing | Alive D2 | Alive D7 | | | Alive D4 | Dead | Alive D2 | Al

Figure 18

Surface inoculation onto PU nanofibers

| MS2 | | Staphylococcus (somewhat fragile) | | Yersinia (very fragile) | |
|---|---|---|---|---|---|
| Day | Log Changed from Day 0 | Day | Log Changed from Day 0 | Day | Log Changed from Day 0 |
| Room Temperature | | | | | |
| 5 | -1.7 | 3 | -0.9 | 3 | > -3.1 |
| 8 | -0.7 | | | | |
| 4 - Refrigerator | | | | | |
| 5 | -0.4 | 3 | -0.8 | 3 | -1.6 |
| 8 | -0.5 | | | | |
| 75% - Humidity Chamber | | | | | |
| 5 | -0.6 | 3 | -0.3 | 3 | > -3.1 |
| 8 | -3.3 | | | | |

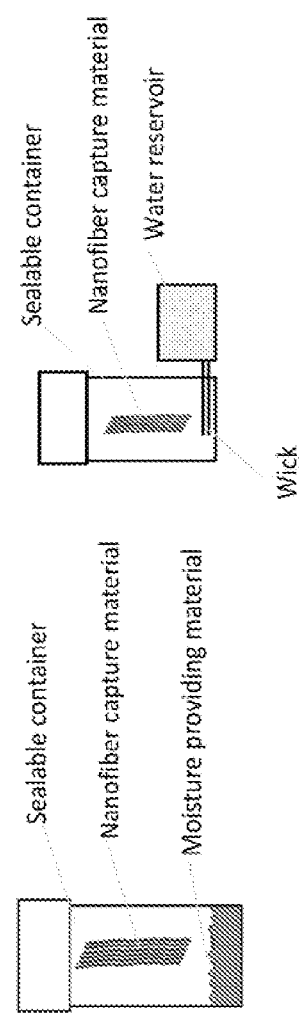

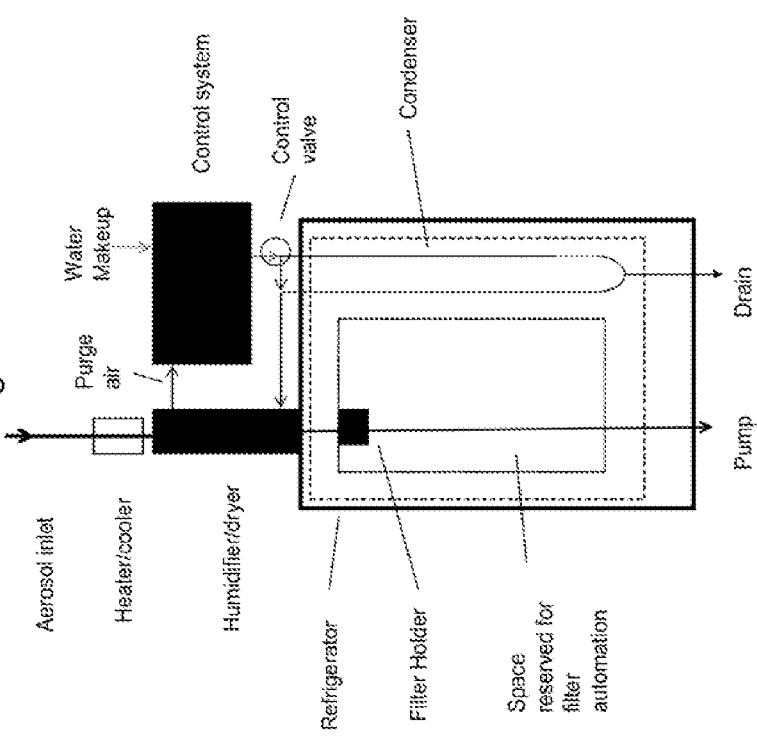

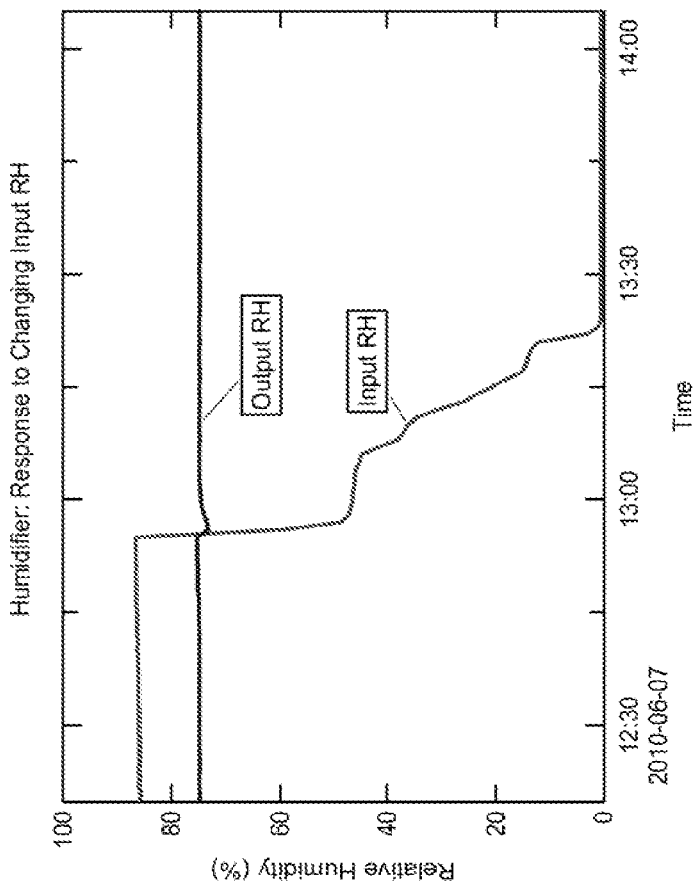

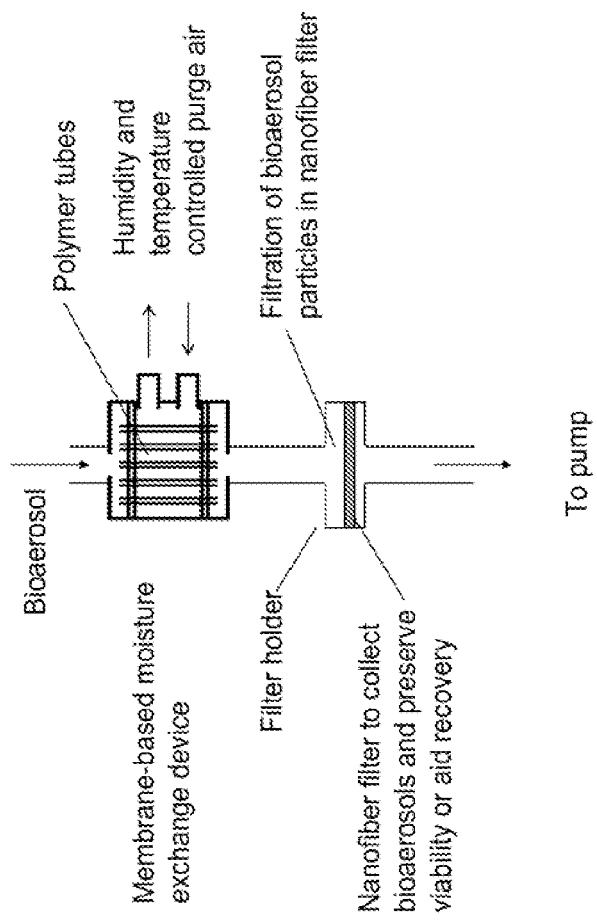

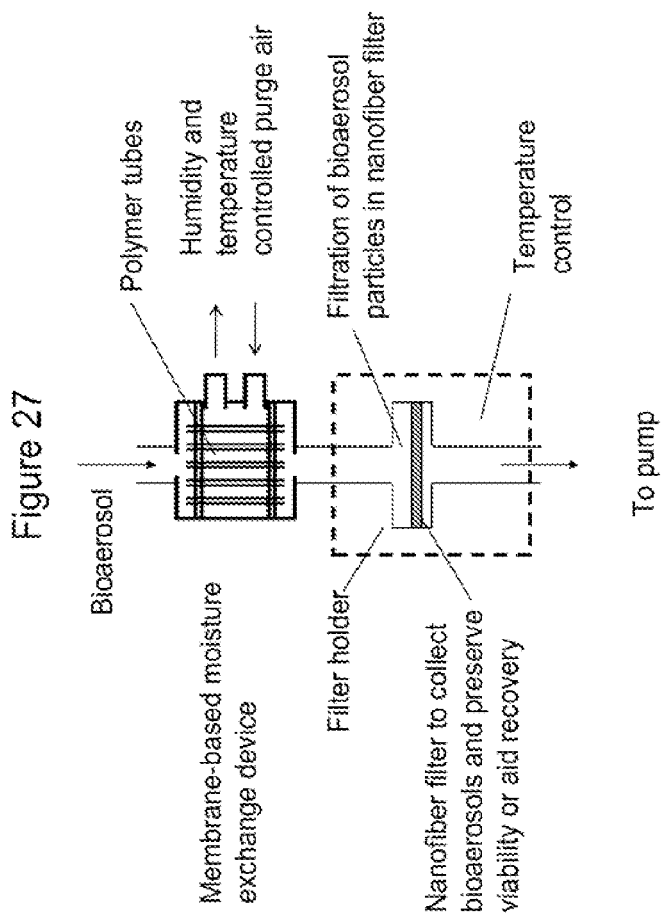

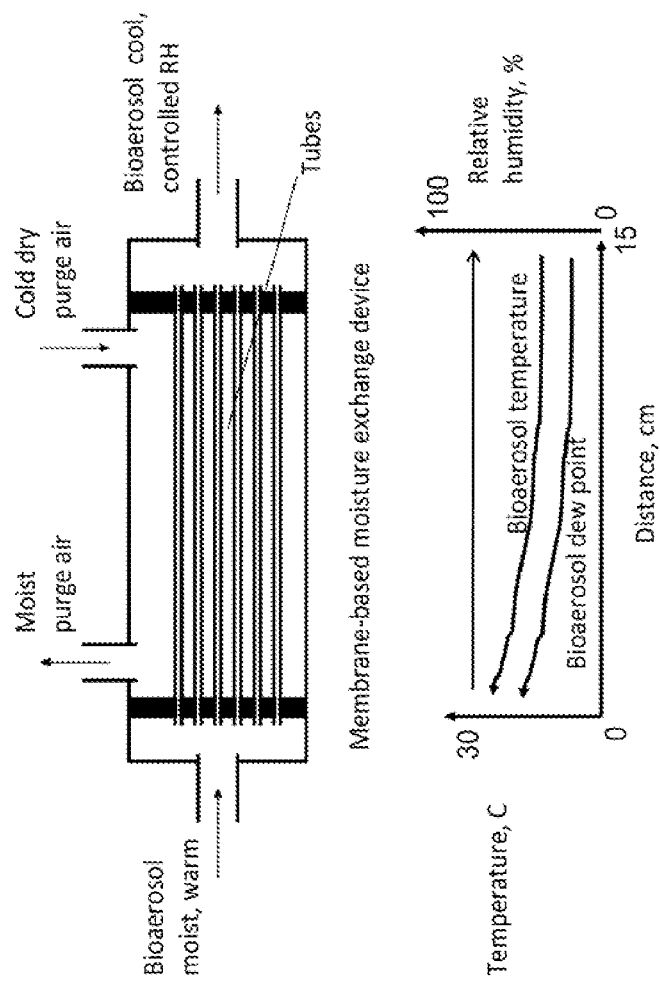

Figure 30

FIBER SAMPLER FOR RECOVERY OF BIOAEROSOLS AND PARTICLES

CROSS REFERENCE TO RELATED APPLICATIONS

This application is continuation application of U.S. Ser. No. 16/455,067, entitled "Improved Fiber Sampler for Recovery of Bioaerosols and Particles," the entire contents of which are incorporated herein by reference, which is a divisional application of U.S. Ser. No. 14/378,768, entitled "Improved Fiber Sampler for Recovery of Bioaerosols and Particles," the entire contents of which are incorporated herein by reference, which is a National Stage Entry of PCT/US2013/026683 filed Feb. 19, 2013, which is related to and claims priority under 35 U.S.C. § 119(e) to U.S. Ser. No. 61/600,366 filed Feb. 17, 2012 entitled "Improved Fiber Sampler for Recovery of Bioaerosols and Particles," the entire contents of which are incorporated herein by reference. This application is related to PCT/US2011/048094, filed Aug. 17, 2011, entitled "Fiber Sampler for Recovery of Bioaerosols and Particles," the entire contents of which are incorporated herein by reference. This application is related to U.S. Application Ser. No. 61/374,466, filed Aug. 17, 2010, entitled "Fiber Sampler for Recovery of Bioaerosols and Particles," the entire contents of which are incorporated herein by reference. This application is related to U.S. application Ser. No. 13/211,940, filed Aug. 17, 2011, entitled "Fiber Sampler for Recovery of Bioaerosols and Particles," the entire contents of which are incorporated herein by reference.

This application is related to U.S. application Ser. No. 11/559,282, filed on Nov. 13, 2006, entitled "Particle Filter System Incorporating Nanofibers," the entire contents of which are incorporated herein by reference. This application is related to U.S. application Ser. No. 10/819,916, filed on Apr. 8, 2004, entitled "Electrospinning of Polymer Nanofibers Using a Rotating Spray Head," the entire contents of which are incorporated herein by reference. This application is also related to U.S. application Ser. No. 10/819,942, filed on Apr. 8, 2004, entitled "Electrospray/electrospinning Apparatus and Method," the entire contents of which are incorporated herein by reference. This application is related to U.S. application Ser. No. 10/819,945, filed Apr. 8, 2004, entitled "Electrospinning in a Controlled Gaseous Environment," the entire contents of which are incorporated herein by reference. This application is related to U.S. Ser. No. 11/130,269, filed May 17, 2005 entitled "Nanofiber Mats and Production Methods Thereof," the entire contents of which are incorporated herein by reference.

STATEMENT REGARDING FEDERALLY SPONSORED RESEARCH OR DEVELOPMENT

This invention was made with government support under HSHQDC-09-C-00154 awarded by DHS. The government has certain rights in the invention.

BACKGROUND OF THE INVENTION

Field of the Invention

The invention is related to fibers, methods, and devices for collection of bioaerosols and particles on fiber structures. The invention is also related to electrospun materials for filtration and air sampling, in particular the collection of bioaerosols.

Description of the Related Art

Collection of both indoor and outdoor air samples is important for monitoring air quality. A wide range of microorganisms are of interest including bacteria, fungi and viruses. From a health standpoint, toxins and allergens may be of interest as well. For example see, J. M. Macher (1999) *Bioaerosols, Assessment and Control*, American conference of Governmental Industrial Hygienists, Cincinnati, Ohio.

More recently, concerns about airborne pathogens being present due to natural processes, accidents, or terrorist attacks has led to the need for improved sampling systems. In addition to the problem of collecting the aerosol (particles) is the problem of recovering the particles for analysis. In the case of biological particles, a common problem is that the organisms die during collection or after collection while awaiting laboratory analysis. Current sampling methods onto microbiological media do not permit extended sampling times beyond 30-45 minutes in the case where preservation of viable organisms is of interest.

In general, a concentrated, viable collect of submicrometer biological particles has been recognized in the art as a challenge. Each bioaerosol sampling method has limitations with respect to sampling time, desiccation, shelf life of sample, complexity, compatibility with analysis via PCR and live recovery. Some evaluations are given by Griffiths and Decosemo (1994); Henningson and Ahlberg (1994); Wang, Reponen et al. (2001); Tseng and Li (2005); Verreault, Moineau et al. (2008); Mainelis and Tabayoyong (2010) listed below:

Griffiths, W. D. and G. A. L. Decosemo 1994. The Assessment of Bioaerosols—a Critical-Review. *Journal of Aerosol Science* 25(8): 1425-1458.

Henningson, E. W. and M. S. Ahlberg 1994. Evaluation of Microbiological Aerosol Samplers—a Review. *Journal of Aerosol Science* 25(8): 1459-1492.

Mainelis, G. and M. Tabayoyong 2010. The Effect of Sampling Time on the Overall Performance of Portable Microbial Impactors. *Aerosol Science and Technology* 44(1): 75-82.

Tseng, C. C. and C. S. Li 2005. Collection efficiencies of aerosol samplers for virus-containing aerosols. *Journal of Aerosol Science* 36(5-6): 593-607.

Verreault, D., S. Moineau and C. Duchaine 2008. Methods for sampling of airborne viruses. *Microbiology and Molecular Biology Reviews* 72(3): 413-444.

Wang, Z., T. Reponen, S. A. Grinshpun, R. L. Gorny and K. Willeke 2001. Effect of sampling time and air humidity on the bioefficiency of filter samplers for bioaerosol collection. *Journal of Aerosol Science* 32(5): 661-674.

The collection of bioaerosols is currently performed by a number of devices that have been available for quite some time. Common bioaerosol sampling devices include:

Impactors where a jet of air deposits the bioaerosol particle on a media surface.

Impingers where the jet of air impinges on a surface within a liquid filled container.

Filters where the particles are collected on the surface of the filter.

Impactors are limited with respect to sampling time because the collection media used to enumerate the number of colonies of organisms for viability after collection is subject to desiccation, thus limiting the sampling time. Also typical impactors designed for microorganisms have a lower particle size collection limit of about 0.5 micrometers.

(Anderson, A. A. (1958) New sampler for collection, sizing, and enumeration of viable airborne particles, *J. Bacteriol.* 76, 471-484)

Impingers are limited in their sampling time from the evaporation of the collecting fluid. The collection efficiency is dependent on the volume of fluid in the impinger. Also the microorganisms may be lost by reaerosolization from the fluid during sampling (Grinshpun, S. A., K. Willeke, V. Ulevicius, A. Juozaitis, S. Terzieva, J. Gonnelly, G. N. Stelma and K. P. Brenner (1997) Effect of impaction, bounce and reaerosolization on the collection efficiency of impingers. *Aerosol Sci. Technol.* 26, 326-342.).

Filters and other collection media such as membranes have long been used to trap aerosol and bioaerosols for subsequent analysis thereof. Filters with a poor figure of merit or quality at least require higher pressures to force air flow through. An example consequence is that in portable samplers operation is severely limited due to battery life in the samplers with filters with high pressure drop. Filter figure of merit or quality is defined as FoM=−log (Pt)/ΔP, where Pt is the penetration of particle at a specific size through the filter and ΔP is the pressure drop at a specific gas flow rate. The larger the FoM, the better will be the performance of the filter. See Hinds, W. C. (1982) *Aerosol Technology*, Wiley, New York, N.Y.). Further, the flow of air through the filters or membranes after a biological aerosol has been trapped can lead to the desiccation of the medium about the bioaerosol and death of the bioaerosol.

Thus, in general, a list of existing air sampling technologies for bioparticles and their drawbacks are provided below.

| Sampler | $d_{50}$ | Typical longest sampling time | Notes |
|---|---|---|---|
| Impinger e.g. AGI-30 | ~0.3 μm | 30 min | Good for short term sampling |
| Impactor e.g. Anderson | ~0.7 μm | 20 min | Collection on agar reduces desiccation |
| SKC BioSampler | ~0.3 μm | 8 hrs | Fluid for long term sampling interferes with PCR |
| Filtration e.g. 37-mm cassette with Nucleopore | * | 60 min[†] | Desiccation is a significant problem with filtration |

* Filtration has a most penetrating size about 0.1 to 0.3 μm with efficiency of collection typically high (>80%) across size range.
[†]Longer term sampling is possible but organisms do not survive.

SUMMARY OF THE INVENTION

In one embodiment of the invention, there is provided an aerosol collection system including a bio-aerosol delivery device configured to supply bioparticles in a gas stream, a moisture exchange device including a partition member coupled to the gas stream and configured to humidify or dehumidify the bioparticles in the gas stream, and an aerosol collection medium downstream from the moisture exchange device and configured to collect the bioparticles.

In one embodiment of the invention, there is provided a method for collecting aerosols. The method includes delivering bioparticles in a gas stream, humidifying or dehumidifying the bioparticles in the gas stream by transport of water across a partition member and into a vapor phase of the gas stream, and collecting the bioparticles by a collection medium.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a table showing sampling challenges for the sampling and preservation of bioaerosols;

FIG. 3 is a schematic showing the collection of bioaerosol particles in a nanofiber filter;

FIG. 4 is a schematic showing a combination of a humidifying section followed by a fiber filter of the invention;

FIG. 9 is Table 1 depicting an example of polymer and surface chemistries studied in this invention;

FIG. 11B is another SEM micrograph showing a cross section of a nanofiber structure formed by deposition of PU on web material;

FIG. 11D is a composite view showing differently scaled depictions of a nanofiber sampling filter in a 37 mm cassette format;

FIG. 13 is Table 2 depicting a comparison of the fiber filter mats of the invention to a standard Teflon filter using the virus MS2;

FIG. 14 is a comparison of viabilities between fiber filter mats of the invention and gelatin and Teflon filters where a bioaerosol of *Serratia* was sampled for 3 hours;

FIG. 15 is a comparison of viabilities between fiber filter mats of the invention and gelatin where a bioaerosol of *Serratia* was sampled, and shows the impact of sampling face velocity on the viability of *Serratia*;

FIGS. 17A and 17B are Tables 3 and 4 depicting organism survivability on different surfaces and different environmental conditions;

FIG. 18 is a depiction showing the storage of the slightly fragile *Staphylococcus* and very fragile organism *Yersinia* at different storage conditions;

FIG. 19 is a schematic depiction of a sample storage device incorporating a moisture providing material;

FIG. 20 is a schematic depiction of another sample storage device incorporating a moisture providing mechanism;

FIG. 24A is a schematic diagram depicting a bioaerosol sampling system of this invention;

FIG. 25D is a schematic depicting humidity conditioning for a single RH-conditioned biosampler;

FIG. 26 is an illustration of the tubular membrane moisture exchanger as used to create controlled relative humidity conditions extending the concept in FIG. 6;

FIG. 27 is an illustration of the applied of controlled temperature and controlled relative humidity for sampling bioaerosols for preservation extending the concept in FIG. 26;

FIG. 28 is a depiction of the tubular membrane moisture exchanger when cold dry air is used to condition warm moist bioaerosol;

FIG. 30 is a depiction of the tubular membrane moisture exchanger when warm moist air is used to heat and humidify cold dry bioaerosol.

DETAILED DESCRIPTION OF THE INVENTION

Figure 2A:
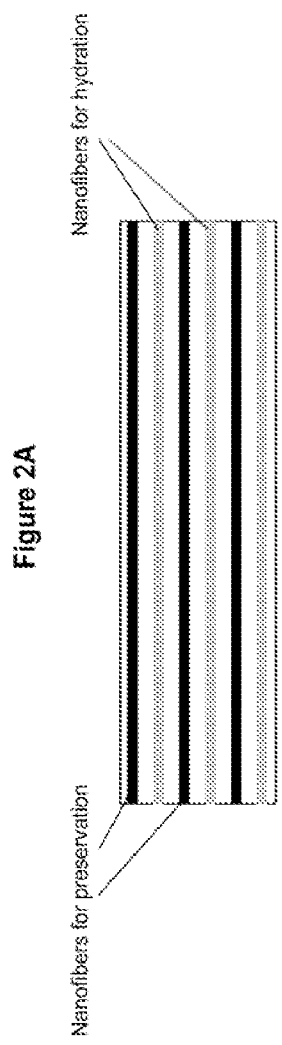
FIGS. 2A and 2B are schematics of fiber structures of the invention.

As described below, this invention addresses collection medium for the capture and storage (under viability enhancing conditions) bioparticles and also addresses three aspects of bioparticle collection and storage which also improve the viability. The particular aspects of bioparticle collection and storage addressed include (but are not limited to):

(1) collection aided by impaction onto nanofiber substrates under controlled relative humidity conditions, as described for example in U.S. application Ser. No. 13/211,940 noted above;

(2) direct filtration (flow-through) with relative humidity RH control but at ambient temperatures; and (3) the simultaneous RH and temperature conditioning during sampling.

As used herein, "bioparticles" means microbes and other biological particles such as for example bacteria, viruses, and biologically derived particles such as proteins, cell fragments, etc.

As used herein, "viable" or "viability" is defined as the capability of having a collected organism becoming active again after being placed into a favorable environment. For example, a collected bacteria spore or vegetative bacterium being placed into a growth media and incubated under appropriate conditions for growth resulting in growth and reproduction of the organism. For example, a collected virus being exposed to its desired host and incubated under appropriate conditions resulting in the virus infecting the host.

As used herein, "collection viability" means the capability to keep a percentage of bioparticles in a collection medium of this invention alive during the collection event.

As used herein, "storage viability" means the capability to keep a percentage of bioparticles in a collection medium of this invention alive from the time of collection until the bioparticles are analyzed or counted.

As used herein, "viability enhancement" or "enhanced viability" encompasses both collection viability and storage viability and means the capability to collect a percentage of bioparticles from a medium without death and keep the collected bioparticles alive until the bioparticles are analyzed or counted.

As used herein, an "osmotic material" is as any material that has the capacity to provide transport of liquids (such as for example water or nutrients) to or from the collected bioparticles. For example, a fiber composed of a hydrophilic polymer would represent on one kind of osmotic material.

As used herein, "design limiting" organisms are organisms which are extremely fragile and extremely difficult to keep alive.

Viable Sampling

In order to determine if an organism is infectious for the purpose of making health related decisions, the viability must be assessed by culture methods where the presence of live organisms at the start of the culture is needed.

Maintaining viability during and after collection is well known to be a challenge. Some organisms are very hardy, such as bacterial spores. These organisms can be very difficult to kill. The same traits that make them difficult to kill make them more readily kept alive or viable during collection and storage. Other organisms are extremely fragile and extremely difficult to keep alive. Maintaining viability of these design limiting microorganisms during collection and during storage is a challenge. Organisms lose viability during collection due to desiccation by either the air moving past these organisms during the collection process or from a process such as evaporation. Also, any condition that leads to an increase in hydroxyl radicals will decrease viability.

Thus, collection of bacteria and virus (microbes) while keeping these bioparticles viable in the case of long term sampling is problematic.

Referring now to the drawings, wherein like reference numerals designate identical or corresponding parts throughout the several views, FIG. 1 details the challenges overcome by the invention for representative organisms important from a health standpoint. More specific, challenges determined by the inventors for conducting long term air sampling, but are not restricted to long term air sampling, in the collection of viable bioparticles include:

Viability during sampling
Sampling duration time
Viability of collected sample during storage
Compatibility of collected sample on the collection medium with analysis techniques.

Bioparticle Sample Collection Devices

Electrospun micro and nanofibers from polymer solutions provide a high surface area environment with tunable surface chemistries which can be conducive to the collection and retention of biological particles. Indeed, the invention in one embodiment provides a sampling device for the collection and recovery of particles, including biological particles such as bacteria, viruses, and yeasts. The sampling device provides for enhanced viability of biological particles and provides for quantitative recovery of samples for laboratory analysis, as detailed below.

The invention provides for a device, based on a fiber mat or a nanofiber mat that provides for collection of bioparticles including bacteria, fungi, viruses, and other biological particles (e.g., bioaerosols). The collection is achieved in one aspect of the invention either through the use of the fiber mat as a filter, for example a high efficiency low pressure drop nanofiber flow-through filter, through the use of the fiber mat as a substrate for impaction of particles, or for the use of a fiber mat as a wipe.

In one embodiment of the invention, the bioparticles are kept viable for extended periods of time (e.g., 1 day to >7 days) without extraordinary efforts because the biological particles are collected in a moisture-rich (or nutrient-rich) fiber mat or nanofiber filter mat. Furthermore, samples can be recovered from the mats for analysis by extraction in buffer or other suitable liquid. Alternately, the fibers can be configured to be dissolved using, for example a low acid or enzymatic solution. Indeed, in one embodiment of the invention, the nano or microfiber material can be constructed from polymers that provide for dissolution in water or an appropriate buffer. Such capability can improve recovery of collected bioparticles for culture and non-culture analysis method such as PCR (polymerase chain reaction), ELISA (Enzyme-Linked Immunosorbent Assay), and a variety of other molecular and biochemical techniques.

In one embodiment of the invention, the fibers are deposited on a variety of backing materials which could include moisture absorbing properties or ability to provide moisture to the fiber mat; for example, super-soaker polymers, hydrophilic polyurethane foam, blotter paper, polymer nonwoven mats containing hydroscopic salts such as lithium chloride, and related methods. Accordingly, the fibers of the invention can form in one embodiment a bioparticle collection device including a collection medium including a plurality of fibers formed into a fiber mat and an osmotic material disposed in contact with the plurality of fibers.

In one embodiment of the invention, the structure and surface chemistry of the fibers, incorporation of additives, or mixed fiber materials incorporating osmotic materials can contribute to the collection and preservation of the bioparticles. Furthermore the container or packaging of the fiber material can aid in preservation. For example, a sealed container containing a hydrogel or other material can be used to maintain RH to aid in viability preservation.

U.S. Pat. No. 4,805,343 (the entire contents of which are incorporated herein by reference) describes for example cellulose acetate hollow fibers that have osmotic properties. Such fibers (or other hydrophilic fibers) could be used in the present invention to provide an external supply of water or nutrients transported to the fiber mats collecting the bio-aerosols. Alternatively, cellulose acetate fibers could be intermixed into the fiber mats collecting the bio-aerosols.

The use of a fibrous matrix to collect and preserve the bioparticles also provides advantages from the equipment design and operation point of view. A long term (>8 hrs) liquid-based sampler typically would require a fluidics system to remove sample and replenish buffers. An RH-controlled fibrous material format would not require as an extensive fluidics system. Furthermore, if a large amount of dust, pollen, and other small particles are present in the fluidics system, then the instrument could become clogged.

A fibrous matrix approach that is free of a fluidics system could tolerate samples laden with dust, but these particles would not shut the system down. Additionally, the mass of liquid needed to operate a system long term could be significantly less. The weight and complexity of a low liquid use or nearly liquid-free sample collection/preservation system could also be much less compared to a liquid collection system.

In one embodiment of the invention, the fibers are deposited on various backing materials, and the combination of the fibers and the backing materials is used as an impaction substrate for collection of the aerosol. For example, the fibers can be electrospun onto a foil and placed as a part of the impaction plate in a standard impactor for air sampling.

The fiber matrix (and especially a nanofiber matrix) provides a high surface area environment for collecting organisms. At the micro-scale of bacteria and viruses, surface chemistry can be important. Using polymers provides for adjustable surface chemistries from hydrophilic to hydrophobic. Furthermore, hydrogels including polymer networks that readily hold water can be used to regulate the moisture content of the nanofiber matrix. Examples of such systems include polymers of acrylic acid combined with sodium hydroxide and co-polymers of poly(2-hydroxy ethyl methacrylate) (polyHEMA). Complex multi-fiber and layered structures can easily be fabricated to provide a mixed environment that cannot be obtained with a liquid system. This mixed environment can potentially provide a way for a variety of organisms that prefer different environmental conditions to exist in the same sample. An example of a mixed environment is simultaneously electrospinning two different polymers onto a common collection substrate thus creating a fibrous mat with two different polymers which would have two different surface chemistries and/or fiber diameters.

In one embodiment of the invention, the fibrous matrix sample collection device includes mechanisms such as those described above or other mechanisms to provide moisture or to maintain the RH in a desired range, for example from 65% to 85% or more precisely 70% to 85% or more precisely 75% to 81%.

In one embodiment of the invention, a polyurethane PU fiber, the structure of the PU nanofibers, the corresponding nonwoven, and the RH all contribute to viability maintenance. In this embodiment, the viability enhancing aspect appears to be only the PU nanofiber mat and surface humidity of the nanofibers, and there is no need for an additional osmotic material, although such an addition could be used.

In one embodiment of the invention, the sample collection device provides viable storage at ambient temperature and RH. In another embodiment of the invention, viability maintenance is enhanced, especially for particularly fragile organisms, via storage at cooled conditions. Storage of fragile organisms such as *Yersinia* has been demonstrated for more than 9 days when stored on a polyurethane (PU) nanofiber media in a laboratory refrigerator.

On one hand, while keeping collected organisms wet may result in germination or growth, and the collection conditions might be good for one class or organisms, the collection conditions might be bad for another class of organisms. On the other hand, an overly dry environment can also kill organisms. A fibrous matrix (optionally combined with other humidity control devices) can provide a relative humidity (RH)-controlled environment to improve preservation of viability of bioaerosols while potentially simplifying sample handling and storage.

Filter Collection Systems

Nanofibers can be used in one embodiment of the invention as a low pressure drop, high efficiency collection filter in any standard sampling form such as the commercial '37 mm air monitor cassette' or other sampling cassette device. (The nanofibers can also be used in an impaction device for example in an eight-stage impactor.)

Figure 2B:
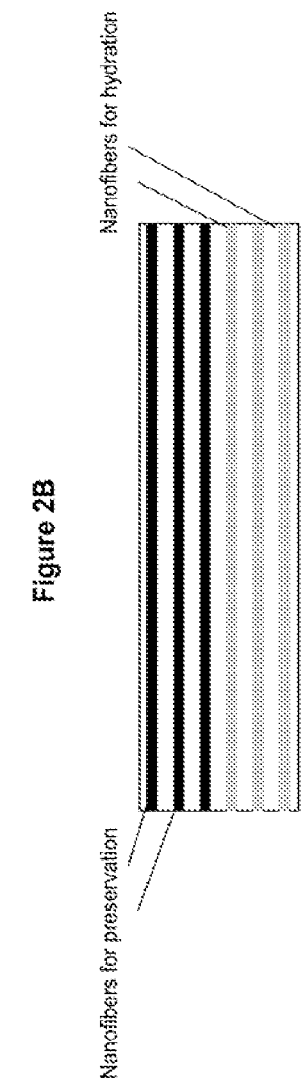

FIGS. 2A and 2B show schematics of various fiber structures. The different fibers designations indicate different function in microorganism preservation. In one embodiment, fibers are present that contain or regulate water moisture. For example, the fibers such as hydrogel polymers or crosslinked polyHEMA or gelatin or similar such material can be used as for hydration. Alternate versions include hydrophilic polymers, like cellulose and its derivatives (e.g. cellulose acetate) and may include incorporation of hydroscopic salts such as lithium chloride; or hydrogel particles, such as those formed from acrylic acid combined with sodium hydroxide, with these particles entrapped in the fiber matrix. In FIGS. 2A and 2B, the white space between the two designated types of fibers represents air space or other fibers in the collection mat (for example having a density and size to promote collection viability and storage viability of a bioaerosol).

In one embodiment, the white space between the two designated types of fibers may be filled with particles which themselves contribute to the viability of the collected bioaerosols. These particles can be introduced during the electrospinning process in a manner as described in U.S. Pat. No. 7,297,305 (the entire contents of which are incorporated herein by reference). For example, particles (e.g., antioxidant particles or nutrient particles) which can contribute to the viability of the collected bioaerosols can be introduced into the fluids suitable for electrospraying and/or electrospinning. Alternatively, these particles can be introduced in a manner as described in U.S. Pat. Appl. No. 2006/0264140 (the entire contents of which are incorporated herein by reference).

In this process, particles which can contribute to the viability of the collected bioaerosols are delivered into a fiber-extraction region of an electrospinning apparatus. The introduced particles collide and combine with the electrospun fiber material during formation of the fibers and the fiber mat. Alternatively, these particles can be introduced after the electrospinning process by flowing a solution (non-reactive with the fibers in the fiber mat and containing the particles of interest) through the fiber mat. The solution can be thereafter evaporated or retained if the solution itself is a substance which can contribute to the viability of the collected bioaerosols.

The fibers in FIGS. 2A and 2B may be aligned or may have random orientations. The fibers in FIGS. 2A and 2B would in one embodiment be in contact with one another in the fiber mat.

In one embodiment of the invention, the hydration fibers are not be required. In one embodiment of the invention, the preservation fibers are not required. When used, the preservation fibers, due to their surface chemistry and structure, promote preservation of the bioparticles. A more detailed description of preserving fibers is provided below.

Accordingly, FIG. 2A illustrates intermixed fiber material made by simultaneous electrospinning onto a common collection plane, and FIG. 2B illustrates the concept of a layered structure that can be formed either by sequential electrospinning to make a layered structure or by spinning from opposing directions to a common plane to simultaneously build to two sides of the composite, layered structure.

As noted above, the fiber mat of the invention can be configured as an impaction substrate or as a flow though filter, and can be used in a variety of air sampling systems and configurations.

Methods of Conditioning Bioparticle Prior to Collection

In one aspect of the invention, the conditioning of inlet air containing bioparticles facilitates the collection of viable bioparticles. In one aspect of the invention, the collection of the bioparticles occurs onto an appropriate substrate (media) that aids in collection of viable bioparticles, aids in storage of the viable bioparticles, and permits analysis via a variety of techniques (e.g. live culture, PCR-based analysis methods, immuno-based assays, etc.).

Accordingly, in one embodiment of the invention, a bioparticle is exposed to the vapor or a working fluid (for example biocompatible fluids such as water). Subsequently, vapor condensation onto bioparticles is induced by either adiabatic expansion or cooling, or by mixing with a cooler airflow.

Accordingly, in one embodiment of the invention, the formed particle-water-condensate bioparticles are collected on the collection medium of the invention.

FIG. 3 is a schematic showing the collection of bioaerosol particles in a fiber filter. The collection in the fiber filter occurs by interception, impaction, and diffusion. In one embodiment, a nanofiber filter has low pressure drop and high efficiency and creates an environment for preservation of microorganisms.

FIG. 4 shows a fiber filter following a humidifying section which controls the humidity at the fiber filter at a target value or range, for example 50 to 85% RH. The humidification chamber (in one embodiment) is disposed at the site of the mixing of humidified air with the bioaerosol sample. The humidification chamber (in another embodiment) is a chamber where water is introduced into the air by wetted porous walls to maintain e.g., a relative humidity of 70 to 80% at the filter.

Figure 5:
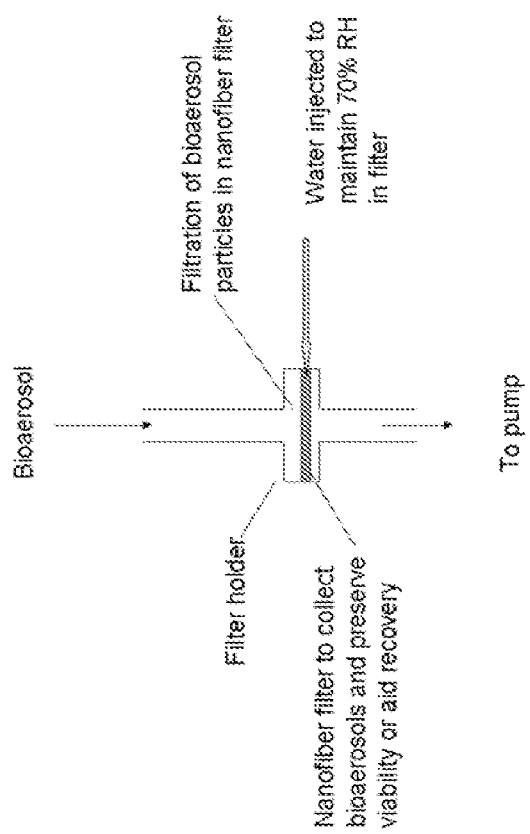
FIG. 5 is a schematic showing the fiber filter with injection of water into the fiber filter to maintain an environment on the filter of 70% RH in this one illustrative example.

FIG. 5 shows the arrangement of introducing water into the fiber filter to maintain an environment e.g. a relative humidity of 70 to 80% which preserves microorganisms during sampling. The humidity would alternatively be maintained during storage.

Figure 6:
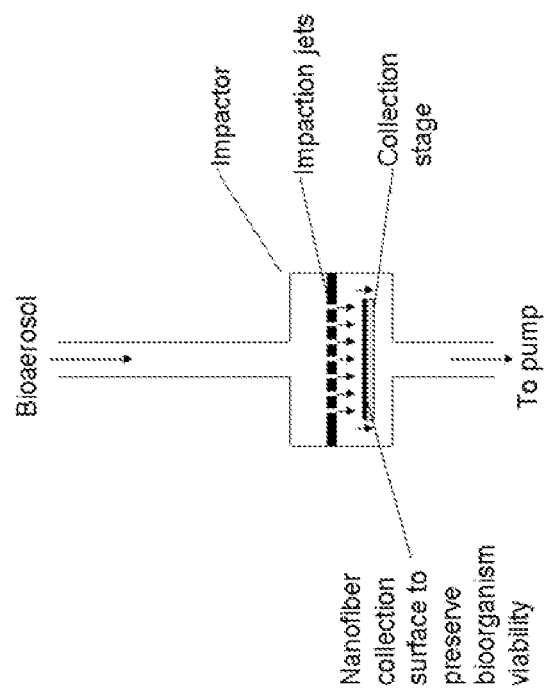
FIG. 6 is a schematic of applying fiber collection surfaces to bioaerosol collection with an impactor.

FIG. 6 shows combination of the fiber with a cascade impactor. The fibers, including nanofibers, prevent rebound of the particles and can provide an environment to preserve the microorganisms. The impactors have small holes forming jets of air directing particles at the collection stage at a high velocity (usually less than 0.3 Mach). The inertia of the particles causes the particles to impact on the fibers.

Figure 7:
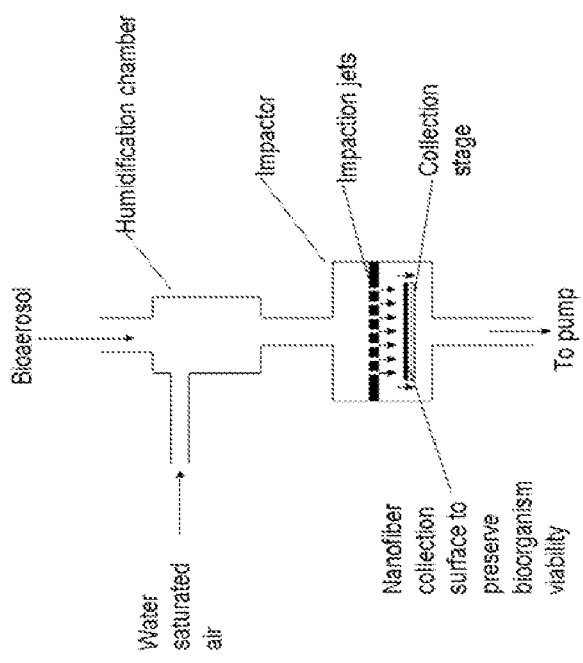
FIG. 7 is a schematic of the combination of humidification of the bioaerosol with an impactor containing fibers on the collection surface.

FIG. 7 shows an impactor containing fiber collection on collection stages with a humidification of the bioaerosol. Humidification (in one embodiment) involves the mixing of the air containing bioaerosol with moist air or (in another embodiment) evaporation of water within the humidification chamber from wet porous walls.

Figure 8:
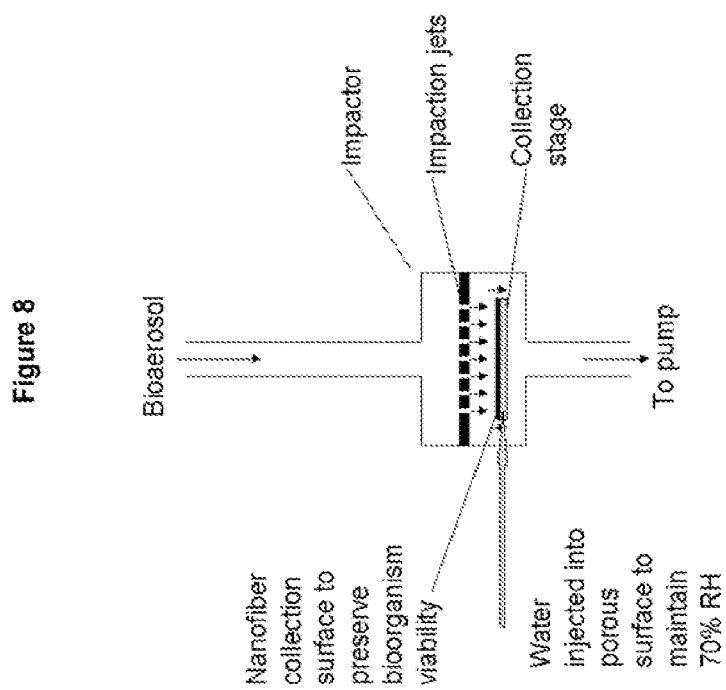
FIG. 8 is a schematic showing a cascade impactor with fiber collection surfaces and water introduction to maintain a controlled relative humidity.

FIG. 8 shows the introduction of water into an impactor with fiber on the collection surface to maintain a controlled humidity e.g., at 70% RH.

Accordingly, in this invention, there are provided a number of ways for conditioning of bioparticles prior to collection, adding water moisture to the sampled air stream, and regulating the relative humidity (RH) of the sampled air stream. Addition of water moisture or regulation of the RH can be achieved via a number of methods including use of a wet walled tube to provide humidity to the sampled air, atomization of water to provide humidity to the sampled air, mixing a wet or dry air stream with sampled air stream to provide air stream at target RH (wet air could be generated through bubbling air through water, a wet walled tube, atomization of water, etc.), and other ways to regulate the RH of a sampled air stream.

Methods of Making Fiber Substrates for Bioparticle Collection

Electrostatic spinning of polymer solutions to form micro and nano diameter fibers, better known as electrospinning, is a ready method to make nonwoven fibrous mats. In one embodiment of this invention, electrospinning is used to make fibrous mats but other methods of fabricating mats of micro and nanofibers may also be a route to form fibrous structures described in this invention. U.S. Pat. Nos. 5,494,616 and 6,520,425; and Badrossamy M R et al., Nano Letters 2010, 10(6):2257 both describe alternative techniques applicable to the invention. The entire contents of these documents are incorporated herein by reference.

A wide variety of polymers can be electrospun into fibers including both synthetic polymers such as polystyrene and natural polymers such as collagen and gelatin. Polymers offer hydrophobic to hydrophilic surface properties including functionalities similar to sugars or proteins. FIG. 9 shows in Table 1 only a limited number of polymer and surface chemistries that are suitable for this invention.

In terms of the use of electrospun fibers for filter mats suitable for the invention, U.S. Pat. Appl. Publ. No. (2005/0224999), the entire contents of which are incorporated herein by reference, describes the use of an electronegative gas to facilitate the electrospinning process by the introduction, for example, of carbon dioxide ($CO_2$) around the spinning orifice or emitter. Gases such as CO, $CF_4$, $N_2O$, $CCl_4$, $CCl_3F$, $CCl_2F_2$ and other halogenated gases can be introduced into the electrospinning environment. These electronegative gases stabilize the Taylor cone formed by the polymer jet as it comes off the needle, reduces corona discharge at the needle, and reduces fiber diameter. Furthermore, spinning in a controlled environment ensures less contamination of the fibers, improves safety, and adds another dimension of control parameters that can be used to fine-tune fiber formation.

An electronegative gas can be passed coaxially with the spinning needle along with use of a controlled gas environment. Typically, a gas shroud is used to provide the coaxial gas flow. A typical shroud can be in the shape of an annulus having an outside radius of about 0.48 cm and an inside radius of about 0.40 cm. Insulating and metallic shroud members can be used. A variety of geometries and sizes are possible; such as for example a circular outside with a hexagonal inside being an additional geometry. In the annular geometry, a distance from an exit end of the annulus where gas is emitted to the tip of the electrospinning element can range from flush (0 cm) to 8 cm; with a typical distance being around 4 to 5 cm, and with the distance being 4.7 cm for the detailed examples later.

Control of the electrospinning conditions has produced polymer nanofibers with an average fiber diameter AFD of 100 nm and less. Nanofibers less than 400 nm have been found to improve the filtration properties of the resultant fiber when combined with other elements of the invention.

Additives in the polymer solution can make a substantial difference in fiber size and quality. Addition of trace amounts of a salt or a surfactant increases the solution conductivity and hence the charge accumulation at the tip of the electrospinning element resulting in larger stretching forces applied to the forming fiber, hence smaller diameter fibers. The surfactant also reduces the surface tension of the polymer allowing for even smaller fibers to be spun. Lithium salts, (for example, lithium chloride and lithium triflate) or surfactants such as tetra butyl ammonium chloride (TBAC) are suitable for the invention. Lithium salt concentrations from 0.01 to 3 wt % are suitable for the invention. Concentrations of TBAC of between 0.06 and 0.4 wt %, were exemplary, although other concentrations are suitable.

Stainless steel extrusion tips from 0.15 mm to 0.59 mm internal diameters (ID) are suitable for the invention. Larger and smaller diameters may also be used. Teflon™ capillary tubes with ID from 0.076 mm to 0.31 mm are suitable for the invention. Larger and smaller diameters may also be used. Both types of orifices can produce small fibers. For both orifices, low flow rates of the polymer solution (e.g., 0.05 ml/hr) coupled with high voltage drops typically resulted in the smallest fiber diameters (e.g., AFD less than 100 nm). In both cases, the voltage was set to 22 kV to 30 kV for a 17.8 cm to 25.4 cm gap (i.e., distance between emitter 2 and mesh 7). Of note is that the voltage per electrospinning-gap is one parameter determining the pulling strength; this gap also determines a travel time thus partly determining fiber stretching time.

Besides stainless steel and Teflon™ extrusion tips, in the invention, other materials (provided the materials are non-reactive with the substance being electrospun including any solvent used in the electrospinning process) can be used such as for example polymers, glass, ceramic, or metal extrusion tips.

The relative humidity RH of the electrospinning chamber effects fiber morphology. For example, when using 21 wt % PSu ($M_w$~35,000 g/mol) in DMAc, a high RH (e.g., >65%) resulted in fibers that have very few defects and smooth surfaces but larger diameters. A defect in a fiber is in general seen as a deviation from a smooth round fiber of long length. Defects thus are beads on the fiber, variations in fiber diameter in the axial direction, etc. A low RH (e.g., <13%,) resulted in smaller fibers but more defects. Modestly low RH (e.g., 40% to 20%) typically produced small fiber size with fewer defects.

A variety of mechanisms are suitable in the invention to control the chamber RH such as placing materials that absorb (e.g. calcium sulfate) or emit water moisture (e.g., hydrogels), operating a small humidifier in the chamber, and adding moisture into the process gas streams prior to introduction to the electrospinning chamber. For example, positive results were obtained by bubbling $CO_2$ through deionized (DI) water and then introducing the humidified $CO_2$ gas into the chamber. In one embodiment of the invention, two gas streams (e.g., one humidified and one dry) are used to obtain a desired RH for the chamber and/or for the gas jacket flowing over the electrospinning orifice.

The fiber diameter obtained in the invention is a function of the polymer molecular weight, the polymer architecture, the solvent or solvents, the concentration of polymer in the solvent system, the additives and their concentration, the applied electrospinning potential, the gap between the spinning orifice and ground, the size and shape of the spinning orifice, the polymer solution flow rate, the flow rate and composition of the process gas that flows over the needle, the RH of the process gas, and the partial pressure of the solvent(s).

Other embodiments of the invention could use different polymer solvent systems and hence different electrospinning conditions to obtain appropriate nanofibers. Furthermore, the same polymer solvent systems could be combined with different electrospinning conditions to create improved fibers or fibers tailored for alternative applications. For example, the jacket of $CO_2$ gas flowing over the needle could contain solvent vapor in order to lower the evaporation rate of the solvent(s) in the polymer jet formed at the needle tip, thus increasing stretching time of the polymer fiber. The partial pressure of the solvent can also be modified via control of temperature, pressure, and mixture of solvents. The solvent concentration as determined by a relative concentration in the atmosphere is controlled to between 0 and 100%.

Filter Support Structures

In addition to obtaining nanofibers having few defects and a close distribution in fiber diameter sizes, the construction of a support and preparation of the surface of the support affect the resultant fiber mat and the resultant filter properties. In one embodiment of the invention, a macroscopic mesh provides adequate support for the nanofibers to withstand the forces exerted on filter mat during filtration and collection of biological medium. The support mesh contributes minimally to pressure drop of the resultant filter.

Filters formed with rigid meshes that contained 1.27 cm, 0.635 cm, or 0.159 cm (i.e., American Engineering standard sizes:½", ¼" and ⅟₁₆" respectively) openings using copper, brass, nickel, stainless steel, and aluminum metal are suitable for the invention. Smaller sizes have also been found acceptable including meshes with openings as small as 0.031 cm. Aluminum window screen with openings about 1.2 mm×1.6 mm is also an acceptable support. The surface of the metal mesh, especially for aluminum meshes, was subjected to cleaning to remove dirt and oils followed by washing the mesh in diluted sulfuric acid (10 to 20% $H_2SO_4$ in DI water by volume) to remove resistive oxides and impurities. This cleaning improved nanofiber dispersion and adhesion. The deposited fibers may not be totally dried of the solvent used to dissolve the polymers. In that state, the fibers adhere to the rigid mesh and after tensioning after drying form a mesh-fiber structure beneficial to reduce pressure drop and increase collection efficiency. Any number of metals or metal alloys, with openings of various shapes (square, rectangle, circular, diamond, oblong and odd shaped), with openings ranging in size from about 12.7 mm down to 1000 times the AFD can be used in the invention.

Adhesion of the nanofibers or fibers to the support mesh can be improved via the application of an adhesive to the mesh directly prior to electrospinning. The adhesive typically is a slow drying adhesive permitting the adhesive to be tacky (i.e., adhesive) when electrospun fibers are deposited. Alternately, in another embodiment, the wires (or components) of the mesh can be coated with a very thin layer of polymer that has surface groups which interact (van der Waals, hydrogen-bond, dipole, electrostatic attraction, etc.) with the polymer fibers being deposited on the mesh. One example system is a thin coating of poly(glycidyl methacrylate) (PGMA) on nickel mesh with nanofibers of poly (methyl methacrylate) (PMMA) deposited on the coated mesh. An alternate embodiment of the invention uses cross linkable systems that are polymerized after the fibers are deposited. Examples include chitosan nanofibers cross-linked with glutaraldehyde and polyvinyl acetate cross-linked with borax; also, deposition of nanofibers on adhesives such as Norland's line of curable adhesives based on mercapto-ester compounds. These surface coatings increase adherence and adhesion of the nanofibers to the support.

The metal mesh can be replaced with metal foams such as ERG's Duocel™ metal foams; for example, Aluminum Durocel with 20 pores per inch (PPI; alternately an average pore size of 1.27 mm). Foams can also be made with copper, nickel, and various other metallic as well as polymeric materials. Porosities ranging from 10 PPI (2.5 mm pores) to 40 PPI (0.064 mm pores) are acceptable for the invention.

The support mesh can be composed of a plastic that is conductive. For example polyester or nylon screen (or coarse nonwoven polymer mesh) is coated with a conductive finish such as gold, palladium, or various metal alloys. The coating process can be achieved by any number of established arts including vacuum deposition (e.g., sputter coating, evaporation deposition, and chemical vapor deposition), and chrome plating of plastics. Alternately, the mesh can be composed of conductive plastic that obtains its conductivity via embedded conductive particles (carbon nanotubes, metals etc.); or, any method to make plastic mesh conductive, semi-conductive, or electrostatic dissipating.

A nonwoven support that is conductive or made conductive (e.g., sputter coating etc., as mentioned above) or moistening with a conductive fluid such as water can be used. The nonwoven support can make a larger contribution to the pressure drop but may be acceptable in certain applications. In certain embodiments, use of woven scrim materials may also be acceptable for a base of a bioparticle collection medium.

The structure of the electric fields between the emitter and ground, which drives fiber deposition, are controlled, in part, by the design of the filter frame holder. Furthermore, the potential of the support mesh can be controlled by an electric field pulsation device (i.e., a voltage limiter or discharge device or an electric field applicator device). The electric field pulsation device can be configured to pulse an electric field at the collector at least once (or frequently) during electrospinning of the fibers to discharge charge accumulated on the electrospun fibers.

Electrospun fibers carry charge to the mesh which is discharged frequently to ground by the voltage limiter device acting in this example as an electric field pulsation device. The resultant electric field is oriented in the direction of the spinning fibers and dynamically modifies the structure of the electric field, thereby imparting improved fiber and mat properties (as measured by the FoM of the mat).

Filters having figures of merit greater than 20 kPa$^{-1}$ for average fiber diameters of the nanofibers less than 200 nm and filters having a FoM greater than 40 kPa$^{-1}$ for average fiber diameters of the nanofibers less than 100 nm have been also realized and are suitable for this invention.

The thickness of the fiber mat can vary from about 0.25 μm (250 nm) to 500 μm or beyond if needed, where most filters had an average mat thickness in the range of 2 to 5 microns. The average mat thickness numbers represent the average thickness of the total fiber mat in a filter. Alternately the mat thickness can be defined as layers of fibers with the thickness including from 4 to 4000 layers where 4 to 400, or 5 to 100, or 5 to 15 layers were typical in various embodiments.

The flexibility of electrospinning even allows mixed polymers such as coaxial, mixed (blended) in same fiber, or deposited as layered or intermixed fibers. In addition to polymer chemistry and mixture of polymers, additives such as salts, proteins, and other materials can be included in the fibers via a variety of methods. These include direct incorporation in the electrospinning solution, deposited or coated onto the surface of the fibers during electrospinning using coaxial spinning, electrospin-spray or co-spinning U.S. Pat. No. 7,592,277 (the entire contents of which are incorporated herein by reference). An alternative to including additives as a part of the spinning process is to use a post-spinning process to coat the fibrous mat. The fibers can be coated after the fibers are formed via depositing the fibers into a liquid bath containing the additives or via dry or wet coating of the fiber mat after it is produced. A variety of these combinations is also possible.

Accordingly, the fibers and nanofibers produced by the invention include, but are not limited to, acrylonitrile/butadiene copolymer, cellulose, cellulose acetate, chitosan, collagen, DNA, fibrinogen, fibronectin, nylon, poly(acrylic acid), poly(chloro styrene), poly(dimethyl siloxane), poly (ether imide), poly(ether sulfone), poly(ethyl acrylate), poly (ethyl vinyl acetate), poly(ethyl-co-vinyl acetate), poly(ethylene oxide), poly(ethylene terephthalate), poly(lactic acid-co-glycolic acid), poly(methacrylic acid) salt, poly(methyl methacrylate), poly(methyl styrene), poly(styrene sulfonic acid) salt, poly(styrene sulfonyl fluoride), poly(styrene-co-acrylonitrile), poly(styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamide, polyaniline, polybenzimidazole, polycaprolactone, polycarbonate, poly(dimethylsiloxane-co-polyethyleneoxide), poly(etheretherketone), polyurethane, polyethyleneimine, polyimide, polyisoprene, polylactide, polypropylene, polystyrene, polysulfone, polyurethane, poly(vinylpyrrolidone), poly(2-hydroxy ethyl methacrylate) (PHEMA), gelatin, proteins, SEBS copolymer, silk (natural or synthetically derived), and styrene/isoprene copolymer.

Additionally, polymer blends can also be produced as long as the two or more polymers are soluble in a common solvent or mixed solvent system. A few examples would be: poly(vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend poly(vinylpyrrolidone), poly(hydroxybutyrate)-blend-poly(ethylene oxide), protein blend-polyethyleneoxide, polylactide-blend-polyvinylpyrrolidone, polystyrene-blend-polyester, polyester-blend-poly(hyroxyethyl methacrylate), poly(ethylene oxide)-blend poly (methyl methacrylate), poly(hydroxystyrene)-blend-poly (ethylene oxide)).

Other embodiments of the invention include the use of polymers that are pH and/or thermal responsive such that the fiber mat can later be modified, respond to a change in environment, or easily dissolved. Example polymers include the commercial pH sensitive polymers know as Eudragit polymers as well as copolymers of N-isopropyl acrylamide (NIPAM) and N-methyacryloy-L-Leucine (MALEU) or (N,N-dimethylamino)ethyl methacrylate (DMAEMA). A similar approach would be to use polymers that are easily degraded with enzymes such as Chitosan which is degraded by Chitosanase and cellulose which is degraded by α-cellulase. Combinations of polymer systems could be used to tune the fiber filter mat properties to the particular application.

Other embodiments of the invention introduce an agent to the fibrous matrix to reduce oxygen toxicity to bioparticles collected in the collection medium. Such agents can be enzymes to reduce oxygen toxicity including catalase. Such agents can be fullerenes and modified fullerenes that have antioxidant properties. In general, substances with known antioxidant properties can be added to the sample collection medium of the present invention to improve viability of the collected bioparticles.

Accordingly, in one embodiment of the invention, fibrous mats can be electrospun that provide favorable conditions for a variety of organisms.

Working Examples of Fibrous Mats for Bioparticle Collection

A variety of polymer fiber mats were prepared for this invention using electrospinning. The polymer solution was prepared to a target concentration in a solvent system amenable to electrospinning. The solution was placed in a 3 ml syringe fitted with a 30G blunt tipped needle and placed into a controlled gas environment (see U.S. Pat. No. 7,297,305, the entire contents of which are incorporated herein by reference) of carbon dioxide and a relative humidity (RH) of 30% to 35%. A high voltage was provided to the needle through an electrical lead to create a voltage gradient of about 1 kV/cm. The polymer flow rate was determined by the electrospinning solution viscosity and ranged between 0.05 to 0.1 ml/hr. The fibers are collected on a substrate depending upon the manner in which the fiber mat was used.

For use as an impaction substrate, the collection substrate was aluminum foil or Whatman filter paper; for use as a flow-though filter, the collection substrate was a light weight nonwoven filter material such as Fiberweb Reemay style 2011, which is a nonwoven filter material with a basis weight of 25.5 $g/m^2$ and an air permeability of 5,650 $L/m^2/s$. In some cases, the nonwoven backing is first coated with graphite, such as by spray painting using Aerosdag G to enhance fiber adhesion to the substrate. The electrospun fiber mat was then rinsed with filtered DI water and dried in a sterile environment overnight to remove any residual solvents. In some cases, additives were coated onto the finished mat in a post-processing step.

One fibrous material prepared was polysulfone (PSu; Udel P3500 LCD by Solvay Advanced Polymers) dissolved in dimethylacetimide (DMAc) at a concentration of 21 wt %. 0.2 wt % tert-butyl ammonium chloride (TBAC) was then added to improve the electrospinning of the solution and the final fiber morphology. The solution was electrospun for 90 minutes at a flow rate of 0.05 ml/hr and voltage gradient of 1.6 kV/cm.

Another fibrous material prepared was polyurethane (PU; Pellethane by Lubrizol) dissolved in dimethylformamide (DMF) at 13 wt %. The solution was electrospun at 1.2 kV/cm and a flow rate of 0.1 ml/hr for 90 minutes. More specifically, Pellethane 2103-90 AE Nat polyurethane (PU) made by Lubrizol, electrospun at about 13 wt % in dimethyl formamide (DMF) to form micro and/or nanofibers was deposited on a backing material. After the fibers are deposited on the backing, the fibrous matrix was flushed with DI water and allowed to dry in a clean environment.

The backing material can be any number of woven or nonwoven media such as spunbound polypropylene. One example is Reemy spunbound polypropylene nonwoven made by Fiberweb. Media with air resistance of 500 CFM/ft2 to 1,500 CFM/ft2 are useful but media with air resistance beyond this range may also be useful. In some cases, using a backing material that is conductive or static dissipating is advantageous. For example, a nonwoven can be spray coated with graphite or coated with conductive material using liquid or gas based (e.g. chemical vapor deposition) techniques. Also materials known in the art that are static dissipating though any number of methods may be useful.

Another example of a nanofiber structure for viable collection and preservation is PU electrospun onto Fiberweb Reemy 2250 that was coated with aerodag (graphite) before electrospinning. The PU fibers have an average fiber diameter of 320 nm, are free of beads, and form a nonwoven mat that is a few microns to 10s of microns thick. Alternatively, the PU fibers can have an average fiber diameter in the range of 100 nm to 280 nm. Alternatively, the fibrous matrix can have PU beads created during the electrospinning process that are 1.5 to 4.5 microns in diameter. In one embodiment, the average fiber diameter is 260 nm, and the PU beads are about 4 microns in diameter. These nanofiber materials with beads about 10 times to 20 times the size of the fibers provide lower pressure drop.

Figure 10:
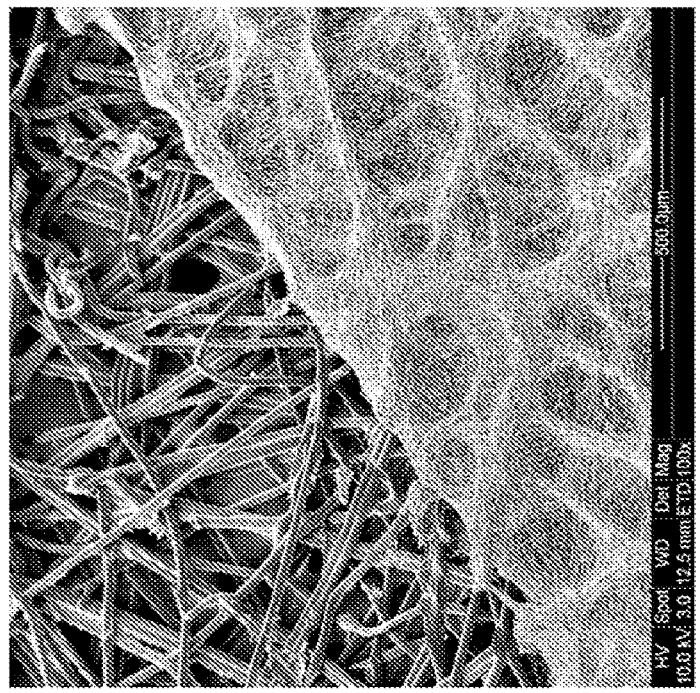
FIG. 10 is a SEM micrograph of a perspective view of a nanofiber structure formed by deposition of PU on a part of a web material.
Figure 11A:
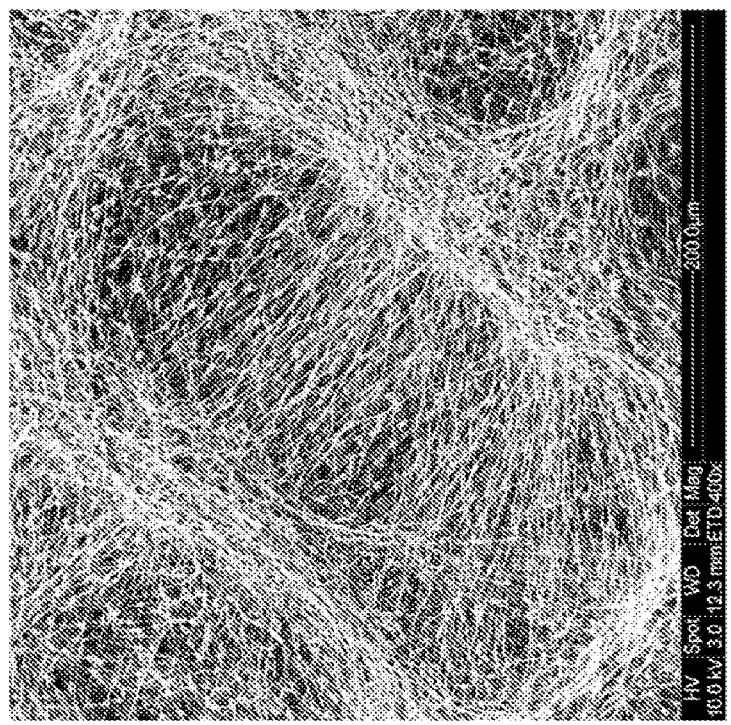
FIG. 11A is another SEM micrograph of a perspective view of a nanofiber structure formed by deposition of PU on web material showing nanofiber coverage and orientation over an opening in the underlying web material.
Figure 11C:
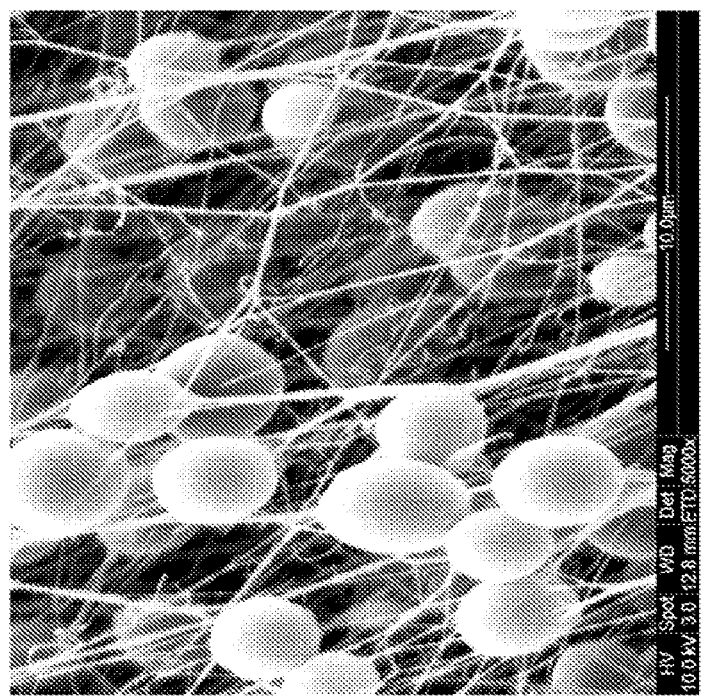
FIG. 11C is another SEM micrograph of a nanofiber structure formed by deposition of PU on web material.

FIGS. 10 and 11A-11C show SEMs of one embodiment of the nanofiber structure formed by deposition of PU on Fiberweb that was first coated with graphite. In FIG. 10, a section of backing material without nanofibers and a section with nanofibers are shown. The nanofibers are supported by the nonwoven backing material. The nanofibers provide for collection of the bioparticles. In FIG. 11A, the beaded structure of the nanofibers and that they oriented between the supporting macrofibers of the conductive nonwoven they are deposited on is evident. This combination of beading and fiber orientation provides a structure that has lower pressure drop compared to other materials. In FIG. 11B, an edge (cross sectional) view of the nanofibers deposited upon the nonwoven backing is shown. The nanofiber layer is 10s to 100s of microns thick, but much thinner than the supporting nonwoven material. In FIG. 11C a high magnification SEM image is shown that indicates the fiber and bead structure. The beads are typically oblong and are 10 to 20 times the size of the fibers. The fibers are on the order of 220 to 280 nm while the beads are on the order of 3.8 to 4.8 microns.

Another fibrous matrix of this invention includes nylon fibers prepared for example from a 15.3 wt % solution of nylon 6 (Sigma Aldrich) dissolved in formic acid. The solution was electrospun at a voltage gradient of 1.6 kV/cm and a flow rate of 0.05 ml/hr for 90 minutes.

Another fibrous matrix of this invention includes polycaprolactone (PCL; Sigma Aldrich, ca 43,000 $M_w$) fibers prepared from a mixed solvent system. The solvent was composed of 80% methylene chloride and 20% DMF. PCL was dissolved in the mixed solvent to a concentration of 18 wt % and electrospun at 1.1 kV/cm with a flow rate of 0.1 ml/hr for 90 minutes.

Another fibrous matrix of this invention includes polystyrene (PS; Sigma Aldrich, ca 350,000 $M_w$) fibers prepared from 23 wt % PS in DMF and electrospun for example at 1.2 kV/cm and a flow rate of 0.1 ml/hr for 90 minutes.

In one embodiment, a fiber-facilitator is used. With a fiber-facilitator (e.g. high molecular weight PEO), nanocellulose and related cellulosic materials can be incorporated in the fibrous matrix to form fibers. In other words, to assist in incorporating cellulose-based materials into fibers, a facilitator which is known in the art (e.g., high molecular weight PEO) to help in the formation of fibers, can be used.

One way according to this invention to impart improved viability maintenance to the fibrous mat was to apply a solution containing additives to the electrospun mat after it was made and rinsed with DI water. The coated mat would then be allowed to dry in a sterile environment. For example, a solution containing a protein containing solution tryptic soy broth can be applied to the mat and allowed to dry before use.

Working Examples of Flow-Through Filters for Collecting Bioparticles

A sheet of nonwoven nanofiber filter media was prepared using PSu as described above with the fibers being deposited on graphite coated fiberweb support material. 37-mm circle filters were punched out of the sheet of nanofiber filter media and packaged into a standard 37-mm air sampling cassettes for testing.

Figure 12A:
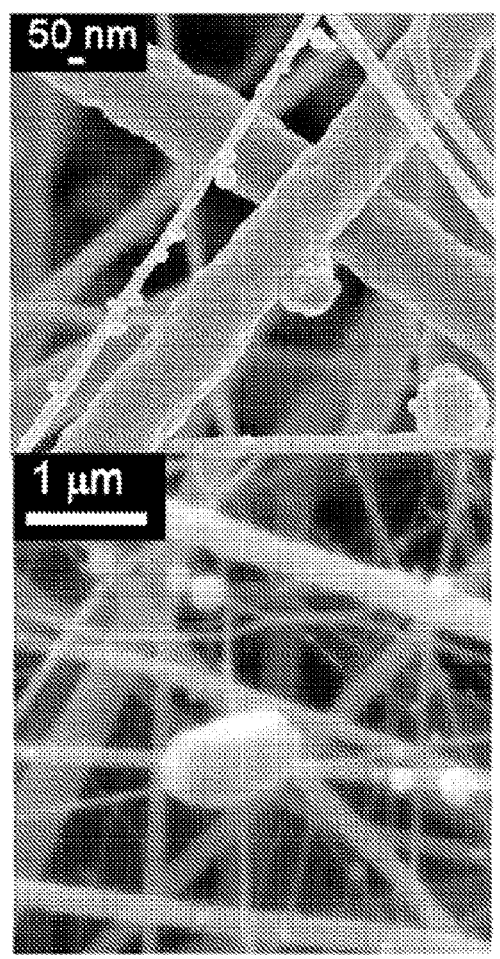
FIG. 12A is a composite of two scanning electron micrograph SEM images showing a collection including a *Bacillus globigii* (Bg) spore and what are likely MS2 virus particles.

FIG. 11D shows a nanofiber sampling filter in the 37 mm cassette format realized by this invention. The efficiency of the filter cassette was measured with 300 nm KCl aerosol particles and was found to be >99.9% and have a pressure drop of 167 Pa for a face velocity of 5.3 cm/s. A similar filter cassette was exposed to bioaerosol, *Bacillus globigii* (Bg) or MS2, and analyzed via SEM and molecular biology techniques. Collection of Bg spores and MS2 particles was obtained. FIG. 12A shows SEM images of a collected Bg spore and what are likely MS2 virus particles.

In one embodiment of the invention, the collection efficiency of the fiber mat structure (sampling filter) formed from a plurality of micro or nanofibers can be >80% and more specifically >95% for particles 0.025 µm to 10 µm in diameter for a flow rate of 25 L/min for a 25 mm sampling cassette. While at the same time, the pressure drop (air resistance) of an unloaded fibrous sampling filter is less than 20 inches of water, and more specifically less than 12 inches of water.

Figure 12B:
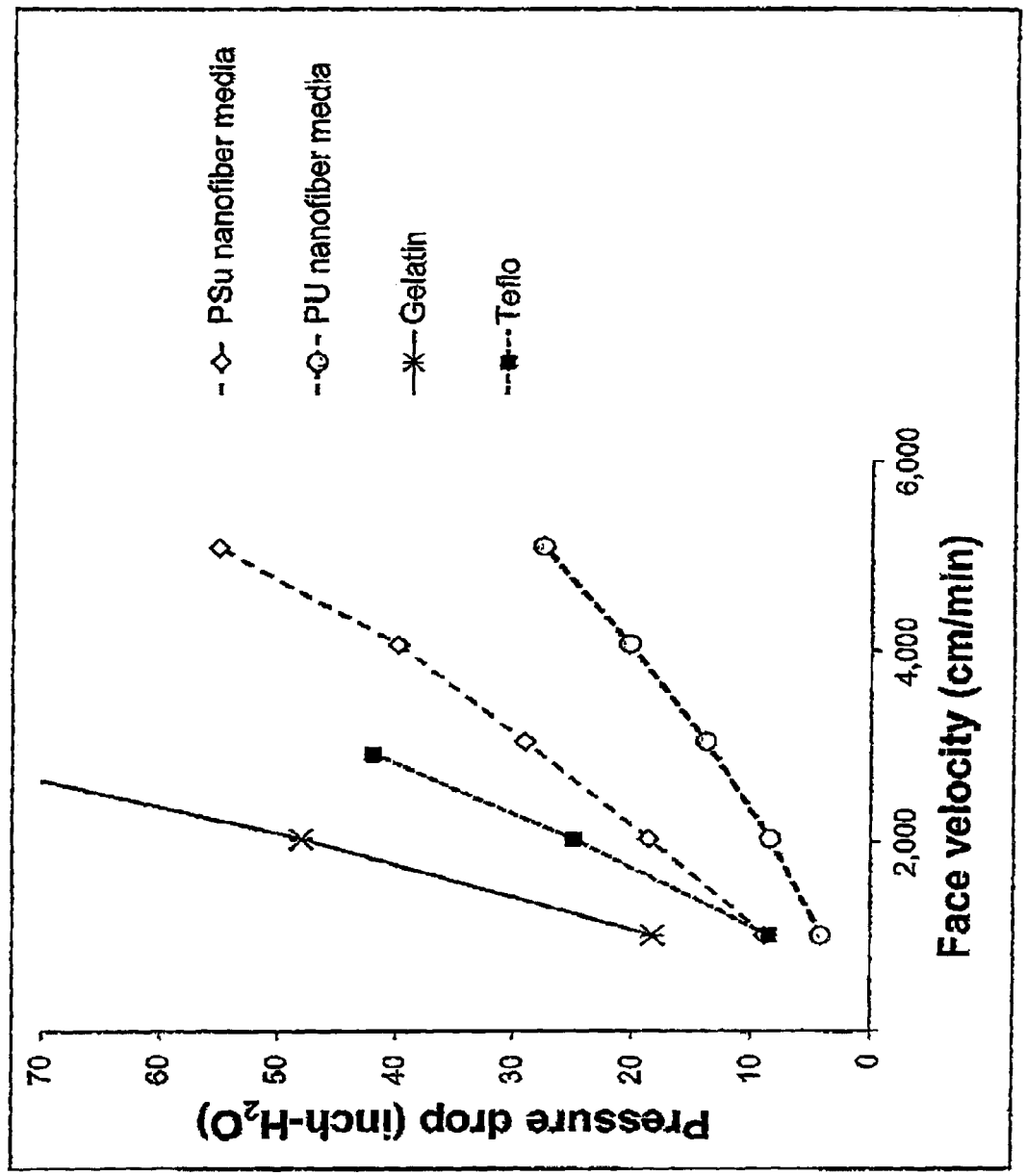
FIG. 12B is a graph of pressure drop curves (pressure drop versus face velocity) for two common commercial air sampling filter materials as compared with nanofiber filter media composed of PSU or PU deposited thereon.

FIG. 12B compares the pressure drop curves (pressure drop versus face velocity) for two common commercial air sampling filter materials with nanofiber filter media composed of PSU or PU deposited on graphite coated fiberweb as described above. The structure formed by the lightweight backing material, the small fiber diameter, the partially oriented fibers, and beaded fibers (exemplified by PU nanofibers) provides for significant reduction in pressure drop. These significantly lower pressure drops of the nanofiber filters translate into advantages for both operation and equipment design. With a lower pressure drop across the filter it is easier to maintain the target RH of the filter and therefore improve viability maintenance of the collected bioparticles. Furthermore, with lower pressure drop the pumps and electrical requirements for an air sampling device are smaller and more cost effective.

Remarkably, despite the efficiency >95% and pressure drop less than 12 inches of water, the sampling filter is able to withstand loading with particles until pressure drops greater than 80 inches of water, and even as high as 100 inches of water.

The fibrous sampling filter described above is able to operate at collection humidities ranging from 10% to 98% with no loss of filtering integrity. However for viability considerations, it is preferably operated in the range of 70% to 85%.

While described here in relation to flow through sampling, these fibrous sampling filters have application in the other sample collection devices described herein.

Bioparticle Collection, Testing, and Evaluation

Viable microorganisms were generated to test the viable collection of the samplers. Bioparticle generation was accomplished though the use of a Collison nebulizer containing a suspension of microorganism. The microorganisms may be suspended in various nebulizing fluids depending upon the organisms and the scenario being tested. Nebulizer fluids range from sterile water to tryptic soy broth with antifoam. The composition of the nebulizing fluids is often selected to simulate the conditions of various bioparticles in the environment as the usual application for bioparticle samplers is to collect microorganism from the ambient or indoor air.

A recognized standard in the art of bioparticle collection is the All Glass Impinger (AGI). The AGI is designed to draw aerosols through an inlet tube (e.g., a capillary tube) to form a jet of the aerosols to be captured by a liquid medium of deionized water or impinger fluid. The jet tip is typically positioned 30-mm above the base of the impinger. The AGI relies on the inertial impaction as a means for collection. However, loss of sampling liquid through evaporation and re-aerosolization of droplets containing virus often reduces collection efficiency of liquid impingers.

The AGI provides collection into liquid for particles larger than about 0.3 microns. Due to the wet collection, the majority of sampled organisms are collected in a viable state. However, this method can only be operated for a short period of time, about 30 minutes. Yet, the AGI is a recognized collection system used as a point of comparison to the fibrous material collection devices of this invention. Andersen biological impactors and the SKC biosampler were also suitable. The liquid collection fluid is diluted (when necessary) and then analyzed.

Sampling of a controlled air stream containing an aerosol of a microbe at controlled concentration was conducted to compare sampling methods. In some cases an AGI is run for 30 minutes in parallel with the other sampling technology with the AGI being considered the "gold standard" to compare viable sampling collection against. For example for a specified test bacteria, 6% of AGI means that the method collected 6% of the colony forming units per liter of sampled air that the AGI collected Meanwhile, the fibrous material collection devices of this invention were suspended in sterile extraction fluid (e.g.— water, phosphate buffered saline, tryptic soy broth [TSB]), diluted and analyzed.

For comparison, the analysis for culturable organisms followed standard procedures where an aliquot of collection fluid, extraction fluid, or a dilution of either, is plated on microbiological media appropriate for the microorganisms collected. The plated media were incubated at a temperature favorable for the microorganism growth and enumerated when colonies (bacteria) or plaques (viruses) are countable.

Evaluation of Collection Via Filtration and Humidity Controlled Filtration

The methods sampling of air using filtration and of adding moisture or controlling the humidity of the sampled air followed by filtration were evaluated using aerosols of bioparticles and comparison with industry standard filtration sampling methods or the AGI.

FIG. 13 includes Table 2 showing a comparison sampling the virus MS2 using filtration without humidity control of the sampled air. The nanofiber filter mats of the invention are compared to a standard Teflon filter. Table 5 assesses both collection efficiency and viability. The collection efficiency of the polysulfone-based nanofiber filter was noticeably higher than the standard Teflon filter or the polystyrene nanofiber filter. (These results are for materials not optimized for a specific microbe collection.)

For demonstration of humidity controlled filtration, a method of controlling the humidity of the sampled air was constructed that measured the RH immediately downstream of the sampling filter. The RH of the sampled air was controlled via mixing with a moist air stream, similar to that shown in FIG. 4. The moist airstream was generated by passing clean, dry air through a bubbler containing deionized water followed by HEPA filtration of the humidified air. The ratio of sampled air to wet air was set at the beginning of the experiment to provide target RH at the filter. This ratio was noted and used to determine the actual volume of air with aerosol sampled from the test chamber containing the aerosolized bioparticles. Various filter types including nanofiber filters of this invention were used. In the art, gelatin filters are recognized as having the best viable collection of commercially available materials. However, when used on their own, as is typical in the art, they too are very limited in the duration time for viable sampling of bioparticles, about 30 to 60 minutes.

Humidity controlled filtration was performed with the vegetative bacterium *Serratia* using nanofiber filters of this invention compared to gelatin or Teflon filters. The nanofiber mats were punched into 25-mm circular filters and placed into a standard 25-mm air sampling cassette. The gelatin and Teflon filters were used as received in a 37-mm air sampling cassette. Bioaerosol was sampled for 3 hours and the results of CFUs of *Serratia* determined. FIG. 14 compares the results of this experiment. The nanofibers and gelatin perform better than the Teflon filters. It should be noted that the gelatin filters have much higher pressure drop than the nanofiber filters, see FIG. 12B.

A similar experiment to that shown in FIG. 12B was attempted with longer term sampling to compare gelatin and PU nanofiber filters for very long sampling times. However, the gelatin filters deteriorated sometime after 3 hours of sampling and collected bioparticles could not be recovered. The PU nanofiber filters were found to withstand sampling times of more than 32 hours of operation.

The impact of sampling face velocity as a function of filter material for RH controlled filtration was tested with 30 minute sampling of *Serratia* as shown in FIG. 15. PU nanofibers and gelatin filters were used with an RH of 75% and the face velocity varied. The PU nanofiber filter is able to collect viable bioparticles at very high face velocities that actually result in rupture of the gelatin filter. As expected the percent viable collected increases with face velocity as more organism per area of filter are collected at the higher flow rates. Operation at high flow rates, as high as 100 L/min or even higher, is desirable for air monitoring. For example release of biological weapon could result in low concentrations of the organism in the air such that sampling as much air as possible to generate as much collected organism as possible is desired (that is as much single collected for the event as possible).

Figure 16:
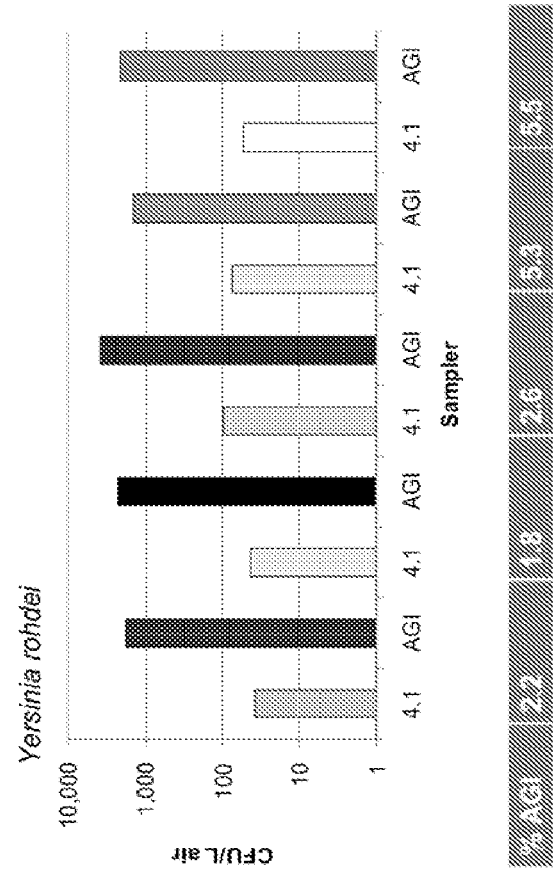
FIG. 16 is a depiction showing of the viabilities obtained when collecting fragile *Yersinia rohdei* using RH controlled filtration with the fiber filter mats of the invention.

To demonstrate collection of a very fragile vegetative bacterium that is particularly difficult to collect in viable form using filtration, *Yersinia rohdei* was collected using RH controlled filtration with PU nanofiber filters compared to an AGI. FIG. 16 shows that indeed collection of even this very fragile organism is possible and repeatable.

RH controlled filtration using nanofibers is an effective way to perform long term viable collection of bioparticles. Using the fibrous material collection devices of this invention provides viable collection similar to gelatin when both substrates are used in the same sampling system and same RH for short periods of time and modest flow rates (face velocity less than 4,500 cm/min). However, the fibrous material collection devices of this invention provide several advantages over gelatin filters: 1) filter pressure drop for nanofibers is much lower for the fibrous material collection devices than gelatin; 2) the robustness of nanofibers in the fibrous material collection devices is much greater than gelatin. The fibrous material collection devices are able to withstand high pressure drops, in excess of 100 inch-$H_2O$, are able to withstand long term operation at >75% RH (e.g., more than 3 hrs, more than 24 hrs). Furthermore, the nanofiber filters are free of contaminants that would interfere with or give false results for microbiology assays.

Storage of Collected Viable Bioparticles

After collection, preserving the organisms is a significant challenge, particularly in the case where samples are not refrigerated.

In one embodiment of the invention, there is provided an automated system for sequential particle collection and storage. In one embodiment of the invention, several days of samples are stored in a single sampling cassette that will also contain an electronic tag indicating individual sample collection times, location, air sampling volumes, and quality assurance (QA) parameters (e.g., flows, operating temperatures, water levels, and other performance parameters). Another cassette can include consumables, including water for the CGT operation or provision of elevated RH by other method and any supplies for sample collection and preservation, depending upon the collection and handling scheme selected. In one embodiment, these cassettes would be exchanged in the field during operation of the sample collector.

As a demonstration, organisms were inoculated via pipetting solution containing microbes onto samples of various nanofiber or fiber substrates and other substrates compatible with air samplers. Two types of inoculations were done to simulate different environmental conditions: "lightly protected" where a buffer with 0.25% TSB in sterile water was used, and "well protected" where a full strength TSB buffer was used. When an aerosol containing microorganisms or other bioparticles is generated in the natural world, it always has other materials with it such as proteins, sugars, sputum, dirt etc that provides protection for the organisms. In a bioterrorist act, the bioparticles would be purposely mixed with protective materials like protein. The samples in this demonstration were stored at ambient temperature (approximately 23° C.) in controlled RH static chamber tests. The relative humidity RH in this demonstration was controlled via saturated salt solutions in the sealed chambers. After storage, samples were extracted in buffer, such as TSB or phosphate buffered saline, and platted on appropriate nutrient media and incubated and organisms enumerated.

FIGS. 17A and 17B include Tables 3 and 4 showing the results of survivability of model organism on various materials. "Alive" means the organism was detected via live culture techniques and "dead" means none were detected. A "D" and number indicated by days of live detection, e.g. D7 means live culture detected at day 7.

In another set of experiments where PU nanofiber filters of this invention were further studied, model organisms were inoculated via pipetting and samples stored under various conditions as shown in FIG. 18. The log change from the day of inoculation (day 0) is reported. Storage of the slightly fragile *Staphylococcus* is possible under a variety of conditions. The very fragile organism *Yersinia* requires storage at cooled temperatures such as 4° C.

Storage of a range of bioparticles on nanofibers is possible. For organisms that are hardy to moderately hardy, storage under conditions not requiring cooling is possible. In some cases storage under humidity controlled conditions such as those provided by the RH control system of the sampled air are sufficient to preserve the collected bioparticles. In the case of fragile and very fragile organisms, cooled storage is required if viability maintenance for more than a day or two are required. As demonstrated, different collection substrates provide viable maintenance for different organisms. With the flexibility of electrospinning and other arts of making fibrous media a mixed polymer fiber environment can be created to provide for viable storage of a broad range of organisms not possible with a single traditional material.

Prior to the invention, the best filter for collection viability that currently existed was a gelatin filter. However, the gelatin filter has a number of problems including contamination and excessive drying during long term sampling without RH control, which both negatively impact the storage viability. Another common filter medium is PTFE (Teflon) filter. Yet, the results above, especially for the design limiting organisms, show that both collection and storage viability and the collection efficiency are enhanced for the fibrous material collection devices of this invention.

The above experiments with aerosolized bioparticles demonstrated that nanofibers are good collectors of microbes (bioparticles). The above experiments show that the selection of polymer and fiber structure is one element impacting viability and controllable by this invention. The above experiments show that preventing desiccation of bioparticles is important is one element impacting viability and controllable by this invention. The above experiments show that viability maintenance can be achieved through incorporation of viability sustaining additives, moisture, etc. and by keeping the fibrous media in an RH regulated environment. These aspects are controllable by this invention.

Alternative Applications

In addition to the collection of bioparticles, the various embodiments of the sampler can collect other aerosol particles of interest to the public health and air monitoring communities. The sampler may be used outdoors to sample ambient air or for sampling indoors in buildings, arenas, or transportation facilities. These filters also offer an advantage because of their semi-transparency for black carbon absorption analysis and low levels of analysis interfering metals.

In these applications, the ambient air samples will contain black carbon or soot from combustion sources, industrial pollution, particles from atmospheric reactions, particles re-suspended from soil and pavements, ocean generated particles and pollen, all of which can be collected by the nanofiber collection devices of this invention. When used for indoor applications, it is expected that the occupant generated particles such as skin cells and residue of personal care products, dust and fibers resuspended from carpets and floors, smoking, and particles introduced from appliances such as electrical motors and heaters or furnaces, and biological material such as toxins and plant or animal debris, all of which can be collected by the nanofiber collection devices of this invention. Aerosol particles collected in the nanofiber filters could be measured by light absorption or reflectance, microscopy, weighing and chemical analysis.

While described above with respect to aerosol sampling, the nanofiber media and aspects contributing to viable collection and maintenance of bioaerosols have applications in the sampling of bioparticles and organisms from surfaces and from water. For example, a wipe or brush or other sample collection device containing the nano or microfiber material described above that provides sample collection and helps viability maintenance could be used to collect bioparticles from a keyboard, lab bench, furniture, vehicle interior, etc. The wipe or brush or other collection device can then be transported with the viability maintenance materials to a laboratory for analysis.

In one embodiment of the invention, the sample collection device can be in the form of wipes, brushes, swabs, sorbent pads, liquid filters, air filters, and/or similar devices for sampling air, liquids, or surfaces. Applications include forensics, regulatory compliance, surveillance, etc.

For embodiments of the invention where the nanofiber material is used to collect microbes without incorporation of mechanisms to control the humidity of inlet air, a container can be used that provides a humidity controlled environment. For example a wipe composed of a plurality of fibers with viability enhancing properties for use in evidence collection. In one embodiment that nanofiber wipe is stored in a sterile container with humidity regulation. In other embodiments the wipe is stored sterile but humidity is not required prior to use. The nanofiber wipe is then used to collect a sample and is placed in the container where the container provides a favorable RH environment for viability maintenance during transport to the laboratory for analysis. The container and wipe thus constitute a sample collection device that provides for viability maintenance.

The samples can then be stored in a sample storage device which can incorporate a moisture providing material or mechanism such as a hydrogel, water saturated salt solution, water reservoir separated from the nanofibers via a moisture permeable membrane providing water transport, or a water reservoir connected to the part of the container holding the nanofibers via a wick. Examples of these are shown in FIGS. 19 and 20. FIG. 19 is a schematic depiction of a sample storage device incorporating a moisture providing material. FIG. 20 is a schematic depiction of a sample storage device incorporating a moisture providing mechanism (e.g., a wick and a water reservoir). The moisture providing material and the moisture providing mechanism can further provide nutrient or antioxidants, as described above.

Local Environmental Control One aspect of maintaining the viability of a collected bioparticle is control of the humidity and temperature conditions of capture and storage. During testing under room temperature conditions, it became clear that various more fragile organisms required cooler than room temperature conditions for storage to maintain viability. Such fragile organisms include but are not limited to Pox viruses, Filoviruses, Arenaviruses, Alphavirus, *Brucella* species, *Burkholderia mallei, Yersinia pestis* and *Coxiella burnetii.*

During a 24 hour sampling period at room temperature and controlled humidity, these organisms when collected in the early part of the period may not survive the full sampling time. These organisms were found to have acceptable recovery for shorter sampler times. In addition, the inventors have found that storage of these fragile organisms on a nanofiber collection medium as described above at room temperature for even a 24 hour sampling resulted in substantial microorganism death.

Figure 21:
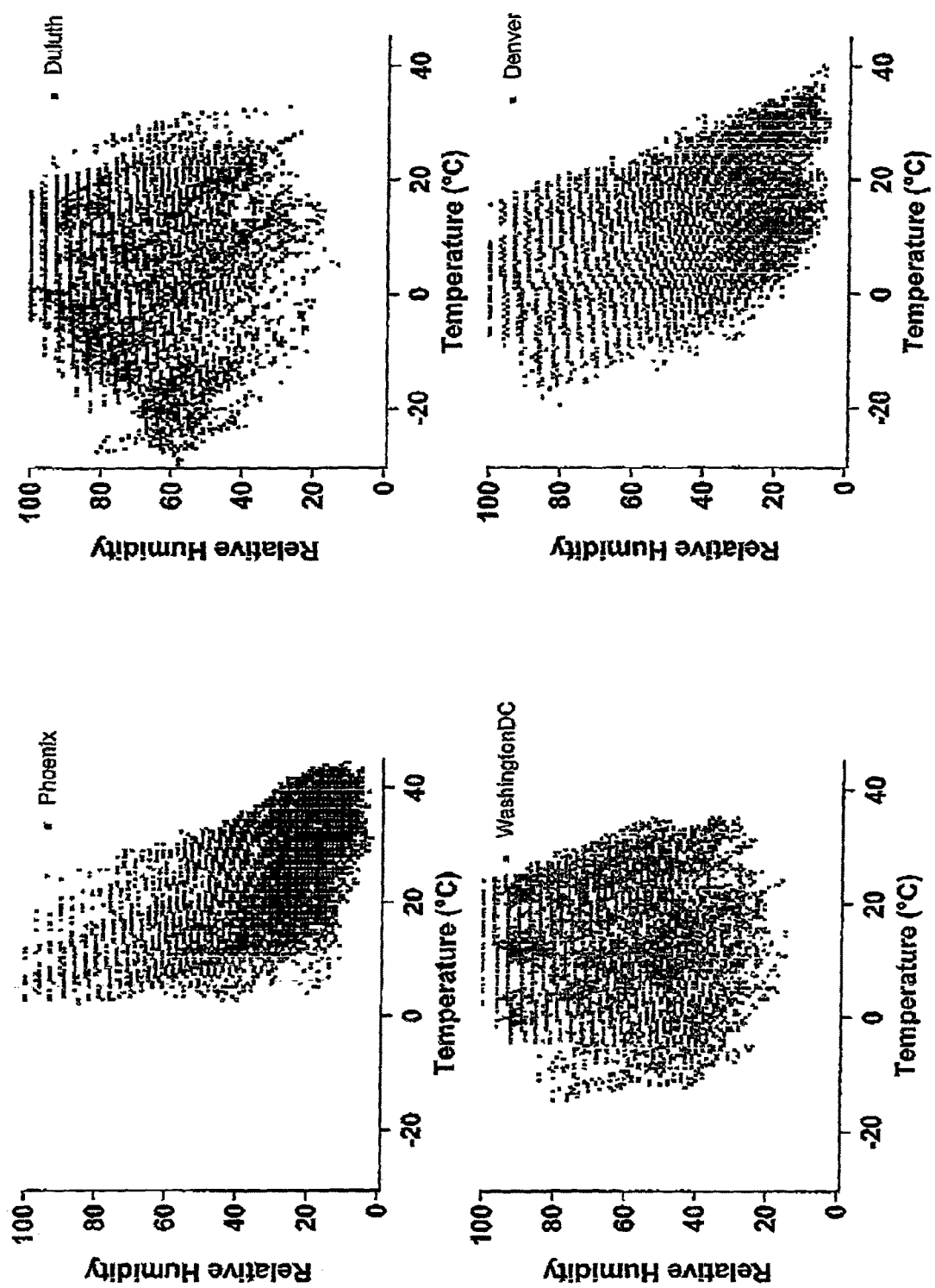
FIG. 21 is a scatter plot of metrological year data showing the range of temperature and relative humidity condition.

Yet, the ability to collect and store the samples on a nanofiber collection medium at controlled, refrigerator-type temperatures, and from wide variety of ambient (and changing) conditions in the atmospheric (ranging from humid summers, dry summers and cold winters) represents a formidable challenge. To illustrate this point, FIG. 21 depicts a scatter plot of metrological year data showing the range of temperature and relative humidity conditions from diverse location climate conditions in the United States of Phoenix, Ariz.; Duluth, Minn.; Washington D.C. and Denver, Colo. While shown for geographical points in the United States, the same challenges occur in sampling around the world.

Described below are techniques and equipment suitable for this invention to promote capture and storage of bioparticles in a local environment (i.e., a contained environment about the collection media) in which the local environment has both below room temperature control and humidity control. In particular, while the invention is not limited to exactly a temperature of 4 EC, a temperature condition of 4 EC has been found to be suitable and useful for both sampling and storage of the collected samples of microorganisms. The description below often refers to the 4 EC condition, but other temperatures and ranges of temperature could be used by the invention dependent for example on the particular microorganism being collected. Suitable temperature ranges for this invention include 2 EC to 6 EC conditions, 1 EC to 7 EC conditions, 4 EC to 10 EC conditions.

Figure 22:
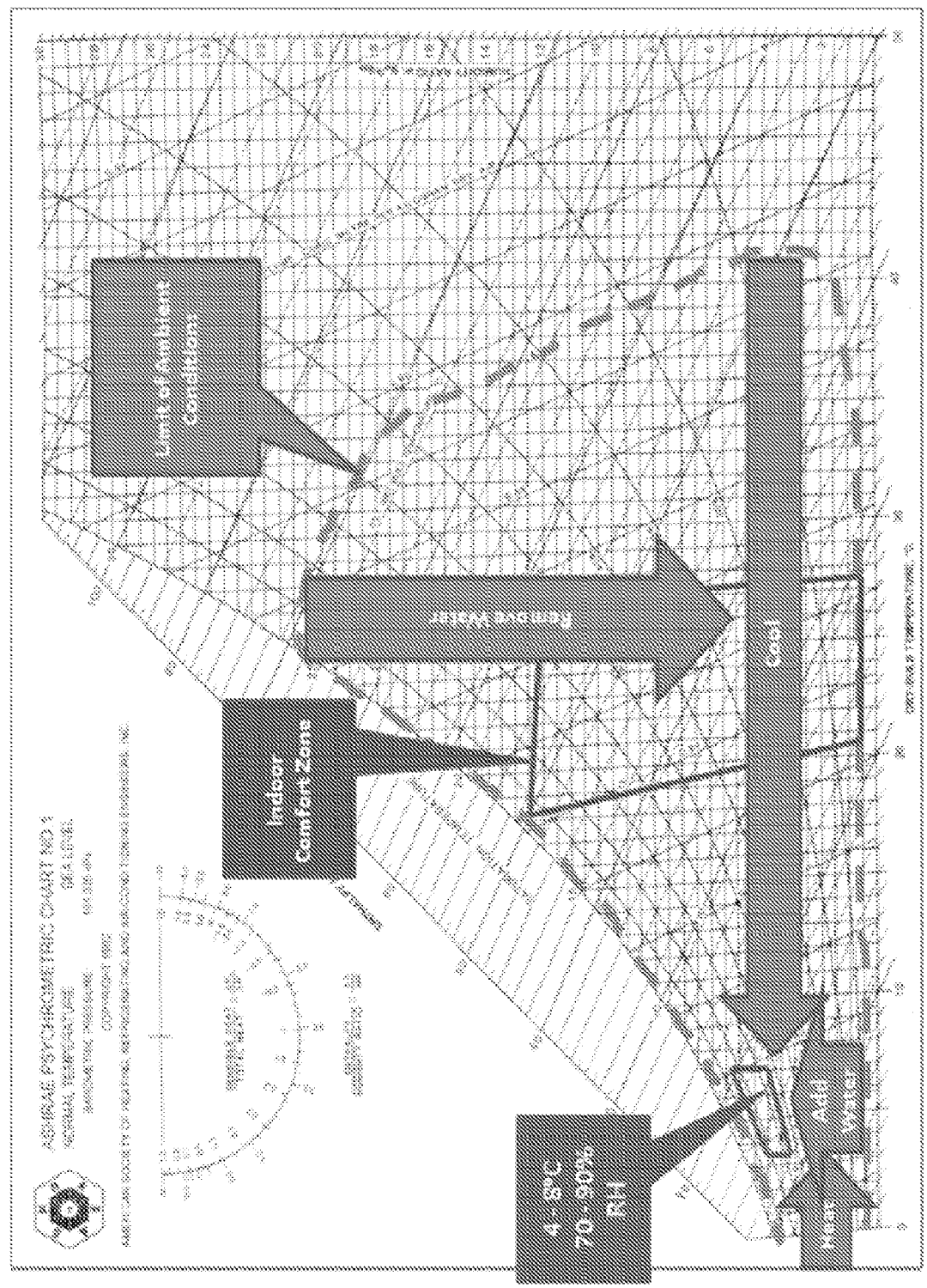
FIG. 22 is a psychrometric chart showing potential ways of conditioning the bioaerosol sample to the ideal sampling and preservation conditions.

FIG. 22 is a psychrometric chart showing potential ways of conditioning the bioaerosol sample to the ideal sampling and preservation conditions at 4 EC and thereby illustrating the relevance of metrological conditions in reaching sampling conditions. The area outlined by the chart in FIG. 22 shows the range of ambient conditions expected for ambient sampling. The rectangle (in the lower left) at 4 EC is the temperature of a typical refrigerator and represents one of the target environmental conditions of this invention for sampling and storage of bioaerosol samples. The challenge is to transport and condition a bioaerosol sample without killing the organisms and while not crossing the saturation line of the chart to prevent wetting of the collection medium and to prevent "washing" of the microorganisms out of the gas stream.

Figure 23:
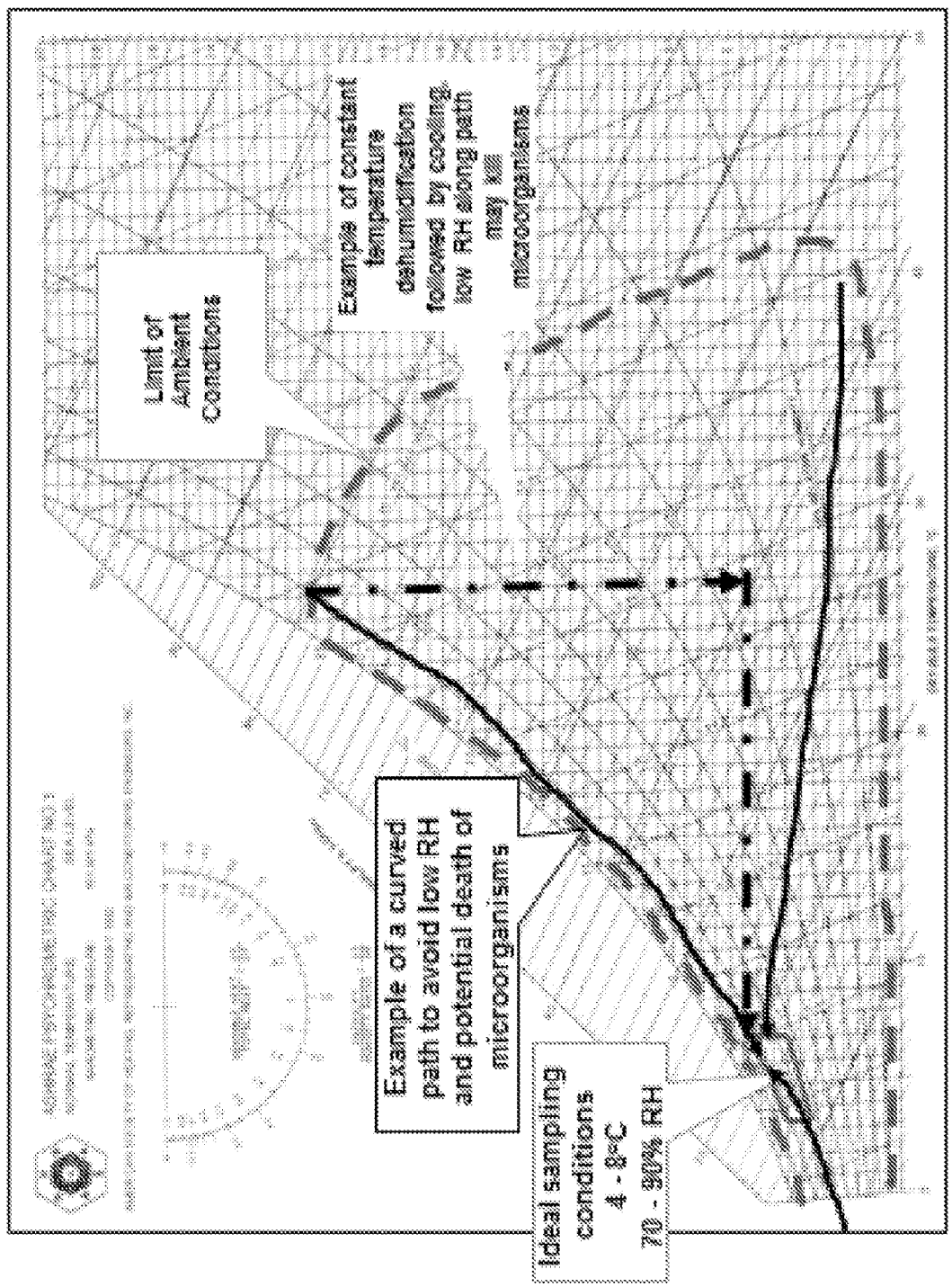
FIG. 23 is a psychrometric chart illustrating preferred paths for conditioning the bioaerosol sample to avoid killing the organisms.
Figure 24B:
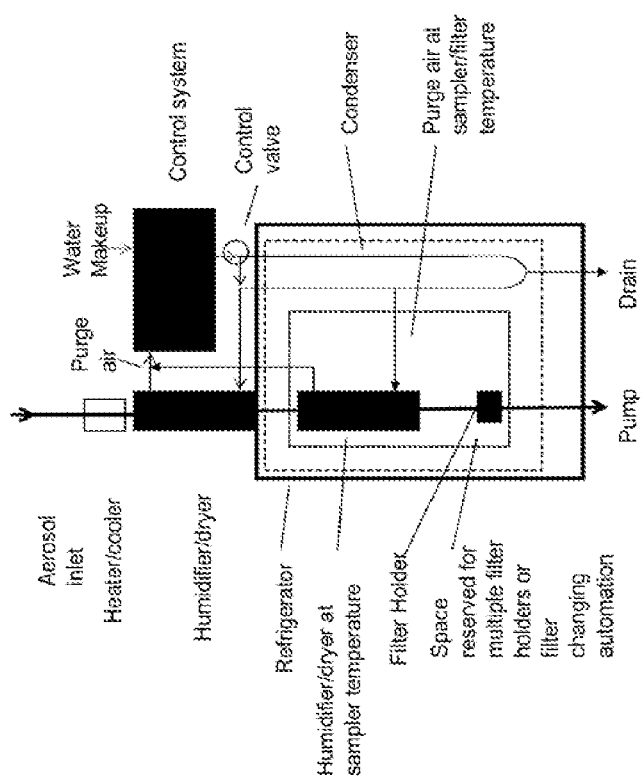
FIG. 24B is a schematic diagram depicting a bioaerosol sampling system of this invention illustrating the principle of multiple or cascaded moisture devices with the final device in the temperature controlled volume at sampler/filter conditions.

FIG. 23 is a psychrometric chart illustrating preferred paths for conditioning the bioaerosol sample to avoid killing the organisms. One preferred path according to one embodiment of the invention would be a path through temperature and humidity space where the survivability of the organisms is not endangered by overheating or overdrying of the organisms. One such path shown in FIG. 23 is along a contour of relative humidity permitting simultaneous heat and moisture transfer to avoid condensation or extreme dryness. The curved path can be replicated through a "staircase" series replicating this control path. A vertical line is shown to depict a path for achieved with adjustment of the absolute water vapor pressure at constant temperature, as done with the apparatus of FIGS. 24A and 25A. Similarly, if one needs to raise either the temperature or the dew point to achieve the target sample temperature and dew point, this can be done by adjusting first the dew point and then the temperature so as not to cross over the vapor saturation line. At a constant temperature the dew point, or relative humidity, can be adjusted to a target value using a (e.g., Nafion™-type) device as shown in the apparatus of FIGS. 24B and 25C. Options such as injecting water sprays for cooling are undesirable because of possible scrubbing and removal of the bioaerosol and contamination from materials in the water. Also, direct contacts with chemical drying materials also have similar problems with contamination.

Also, direct contacts with chemical drying materials also have similar problems with contamination. A vertical line is shown to depict a path for drying with a conventional (e.g., Nafion™-type) device because dehumidification in a conventional device is conducted under a nearly constant temperature.

The invention provides in one embodiment an aerosol collection system including a bio-aerosol delivery device configured to supply bioparticles in a gas stream, a moisture exchange device including a partition member coupled to the gas stream and configured to humidify or dehumidify the bioparticles in the gas stream with a vapor of a biocompatible liquid, and an aerosol collection medium downstream from the moisture exchange device and configured to collect the bioparticles. The moisture exchange devices or units of this invention can include at least one of a permeable material, a semi-permeable membrane material, or a polymeric ionomer.

The addition of a Nafion-type moisture exchanger as shown in FIG. 26 provides for control of relative humidity for bioaerosol sampling which can be controlled in the manner noted above. FIG. 26 illustrates a schematic of a common way of implementing moisture exchange as manufactured by the Perma Pure LLC company. The Nafion is formed into small diameter tubes. These small diameter tubes are sealed into a manifold top and bottom to allow of treatment bioaerosol through the device. The small diameter tubes are mounted as a bundle in a larger tube with side penetrations to allow the flow of moisture containing air for exchange with the bioaerosol within the tubes.

The illustration of the inlet and outlet plenums shown in FIG. 26 shows the principle that bioaerosol entering through a single tube must be transported to a multitude of small diameter tubes for rapid moisture exchange. At the exhaust of the tubes, the flows must be recombined for transport through a single tube. Bioaerosol are composed of discrete particles generally in the 0.1 to 10 micrometer particle size range.

The moisture exchange units used in this invention (such as the Nafion™-type units noted above) have been designed for minimum turbulence in the plenums by eliminating abrupt expansions and contractions of air flow and provide for aerodynamic entry into the tubes by increasing the radius of curvature of the tube inlets to reduce loss of bioaerosol particles. Another way of collecting bioaerosol could utilize tubular membrane moisture exchanger as well.

In FIG. 27, the principle of controlling both the relative humidity and temperature is illustrated. A temperature controlled environment is used to contain the bioaerosol sampling device such as nanofiber filters. The temperature controlled environment may also contain the tubular membrane moisture exchanger as well.

According to one embodiment of the invention, as noted above, the preferred conditioning path would not penetrate the dew point and form liquid water. The inventors have discovered a controlled path existing between excessively low relative humidity avoiding organism desiccation and excessively high relative humidity leading to water condensation.

FIG. 24A is a schematic diagram depicting a bioaerosol sampling system of this invention. The bioaerosol enters the top of the system. A heater/cooler unit is need for either hot or cold conditions. Potentially, this heat exchanger could be a liquid circulation system using the refrigerator than the thermal source. The bioaerosol next enters Nafion™ gas phase water exchanger. FIG. 24B is a schematic diagram depicting the principle that multiple moisture exchange (humidifier/dryer) devices can be employed in series and can be located in the temperature controlled space.

Nafion™ (a polymeric ionomer) is a copolymer of perfluoro-3,6-dioxa-4-methyl-7octene-sulfonic acid and tetrafluoroethylene (Teflon®) in a class of materials called polymeric ionomers. In simpler terms, Nafion is a Teflon backbone with occasional side chains added of another fluorocarbon. The side chain terminates in a sulfonic acid ($-SO_3H$). With the use of Nafion in dryers or humidifier, the Nafion functions essentially as a highly selective, semi-permeable membrane to water vapor. If gases inside the Nafion tubing are wetter than gases surrounding the tubing, drying will occur. If the surrounding gases are wetter, humidification will occur.

Figure 31:
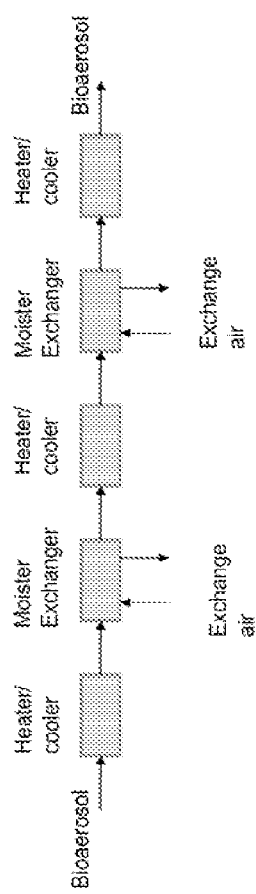
FIG. 31 is a depiction of cascade of heater/coolers and tubular membrane moisture exchangers to control the temperature and relative humidity of the bioaerosol to compensate for water condensation or undue dryness.
Figure 33:
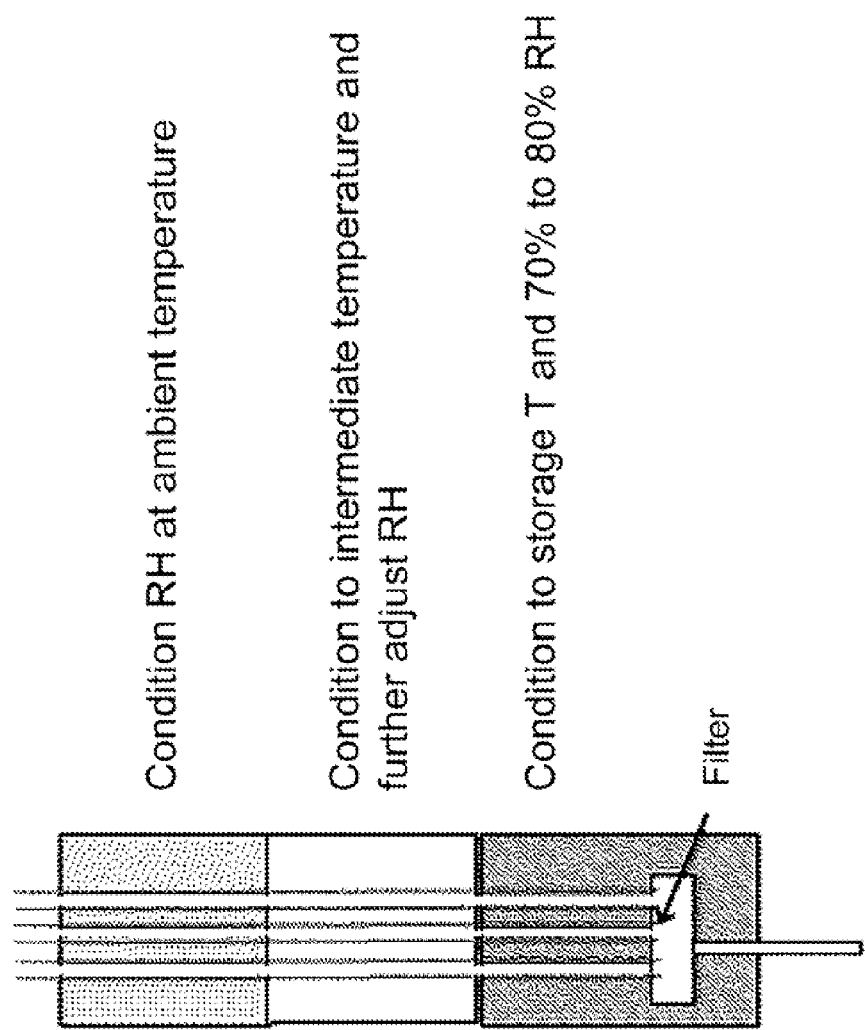
FIG. 33 is an illustration of another cascade of conditioning steps to control the temperature and humidity of the bioaerosol to compensate for water condensation and undue dryness, showing pathways for the aerosol with minimum expansion and contraction of the flow to prevent bioparticle losses.

In this invention, a bioaerosol sample flows through the inside of the semi-permeable membrane tube side while a conditioning gas flows on the shell side. The amount and direction of water transport through the semi-permeable membrane wall depends on the water gradient between tubes and shell. Multiple, moisture exchangers could be used in a cascaded series as shown in FIG. 31. FIG. 33 illustrates the cascading of conditioning steps in a concept to reduce the loss of bioparticles to the wall from excessive expansion and contraction from the flowing bioaerosol. Other semi-permeable polymers beside Nafion can be used. Suitable water vapor-permeable materials for this invention include polymer nonelectrolytes (such as polyethylene oxide, polyvinyl alcohol, cellulose ether and starch) and copolymers thereof; polymer electrolytes (such as polyacrylic acid, polyacrylamide, polyisopropyl acrylamide, polystyrene sulfonic acid, polyvinyl pyridine and polyamino acid) and copolymers and salts thereof; and conventional water-absorbing resins and conventional water-containing resins. Also, it is possible that flat sheet membranes can be used in some applications rather than tubes. In those applications, the bioaerosol particles would be partitioned off from the humidified or dried air by at least one wall of the semi-permeable membrane.

In one embodiment of the invention, a bioaerosol sampling filter is held in the refrigerator section of the bioaerosol sampling system. The sampling filter (as described above) can be made of nanofiber material to improve preservation and allow sampling at a high face velocity. Also, multiple filter holders with a common inlet plenum and controlled with a multi-port valve to allow obtaining single day samples over several days can be used. The refrigerator section of the bioaerosol sampling system can also be used as a source of cold dry air. An external refrigerator or dehumidifier (not shown) could also be used as a source of cold dry air.

The control system depicted as a box in FIGS. 24A and 24B regulates the water vapor removed or added by controlling the water vapor content in the shell side flow of the Nafion water exchanger. A condenser is shown to indicate that removal of water from the shell side flow from the Nafion water exchanger might be accomplished by cooling. Multi-day sampling might be accomplished by the use of multiple sample holders with flow switched with a multiport valve or by automated filter changing. It is expected that these schemes would be contained within the refrigerator section of the bioaerosol sampling system.

Figure 25A:
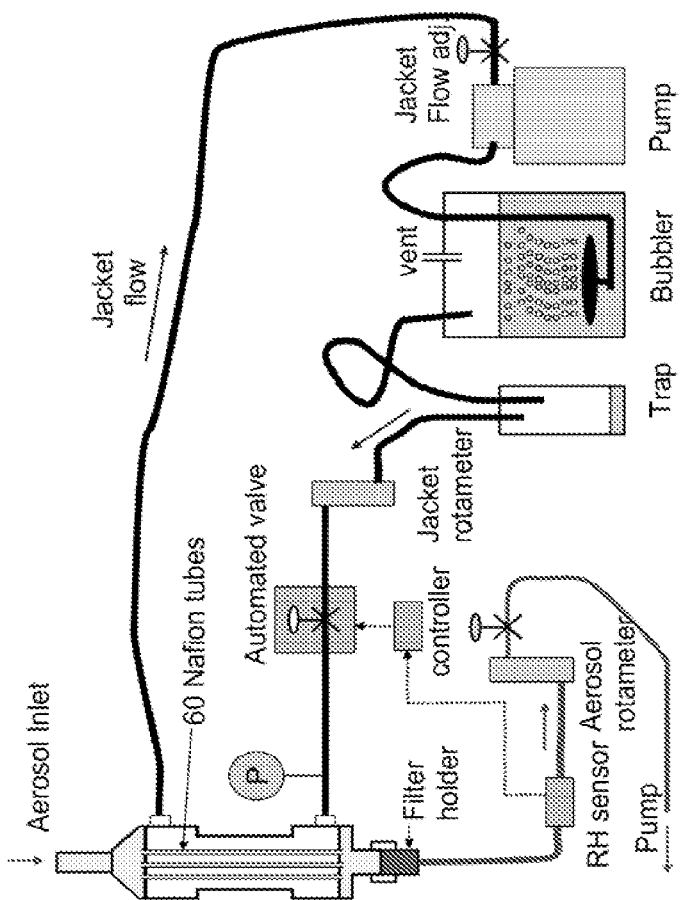
FIG. 25A is a depiction of a humidity control system of this invention.

Control of the relative humidity at the point of sampling at ambient temperature can be accomplished with the system of FIG. 25A. One key is to either humidify, or dehumidify, as needed to bring the sample flow RH to 75% to 85% upstream of the point of collection. FIG. 25A is a depiction of a humidity control system of this invention. The specific system pictured in FIG. 25A adjusts the RH to the target RH at the sample temperature. Regulation of the total pressure of the humidified air flow in the shell side of the Nafion system provides a mechanism for adjusting the relative humidity of the sample flow. The shell side refers to the interstial space between the Nafion tubes that carry the sample flow. Typically, the shell side flow rate carries a counterflow at a mass flow rate equal to about twice the sample flow. This Nafion-based relative humidity conditioner adjusts the relative humidity of the sample stream to the target relative humidity, either humidifying or dehumidifying as needed, by controlling the absolute pressure of water vapor in the shell side. This absolute pressure is controlled by adjusting a valve immediately upstream of the inlet to the shell. The flow through this valve creates the pressure drop, and thereby controls the absolute pressure of water vapor in the shell side. The system in FIG. 25A in one embodiment is designed to humidify air to 70% RH at a constant temperature. The system either humidifies or dehumidifies by controlling the pressure of highly saturated air flow in the shell region. When the shell pressure is near atmospheric pressure, the dew point of the shell flow is also high and this brings the RH of the sample flow to a high relative humidity. When the pressure of the highly saturated air flow in the shell is at a reduced pressure, perhaps as low as one-half of an atmosphere, the dew point is likewise reduced because the absolute pressure of water vapor is reduced along with the total pressure. If the shell dew point is lower than the sample dew point the system Nafion system will dehumidify. The control of the pressure in the shell region, and hence the RH achieved, can be controlled automatically through the adjustment of the valve based on the reading of the RH at the sample temperature. Thus both functions of humidification or dehumidification are incorporated in the same apparatus.

In one embodiment of this invention, the membrane-based moisture exchange devices are tube in shell devices. This geometry creates a barrier between the bioaerosol and the conditioning air preventing contamination. Conventionally, Nafion™ systems are used at constant temperature. In the present invention, if cold air at 4 EC were introduced at the bottom port on a Nafion-type moisture exchanger in FIG. 25B, then a temperature gradient would exist up the axis of the device. Although not a primary consideration for bioaerosol conditioning, reducing the temperature of purge gas or jacket flow has the additional advantage of improving the ability to reduce the dew point of the conditioned gas.

Figure 29:
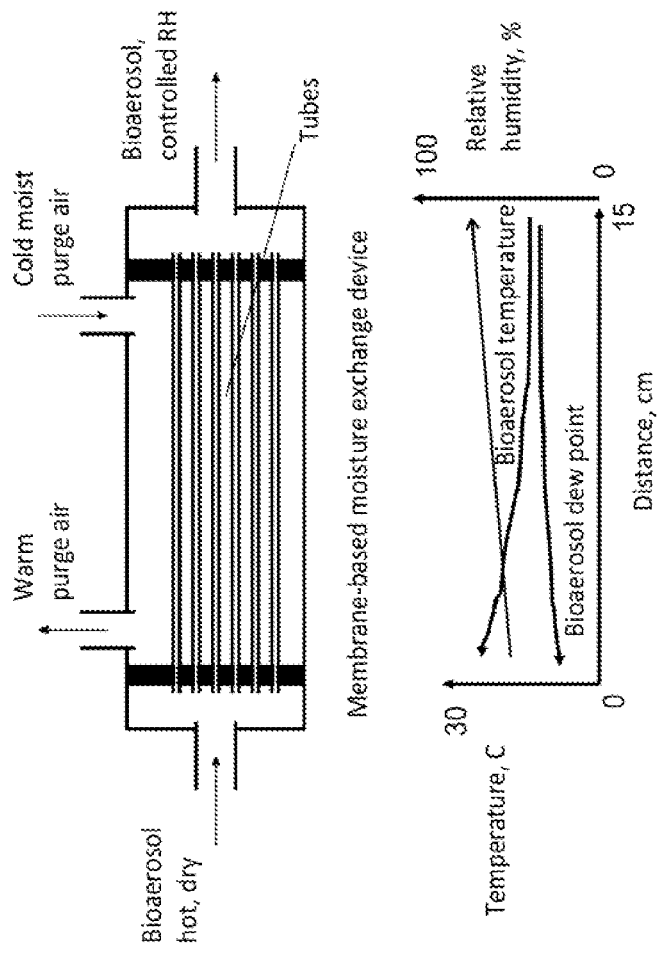
FIG. 29 is a depiction of the tubular membrane moisture exchanger when cold moist air is used to cool and humidify hot dry bioaerosol.
Figure 30:
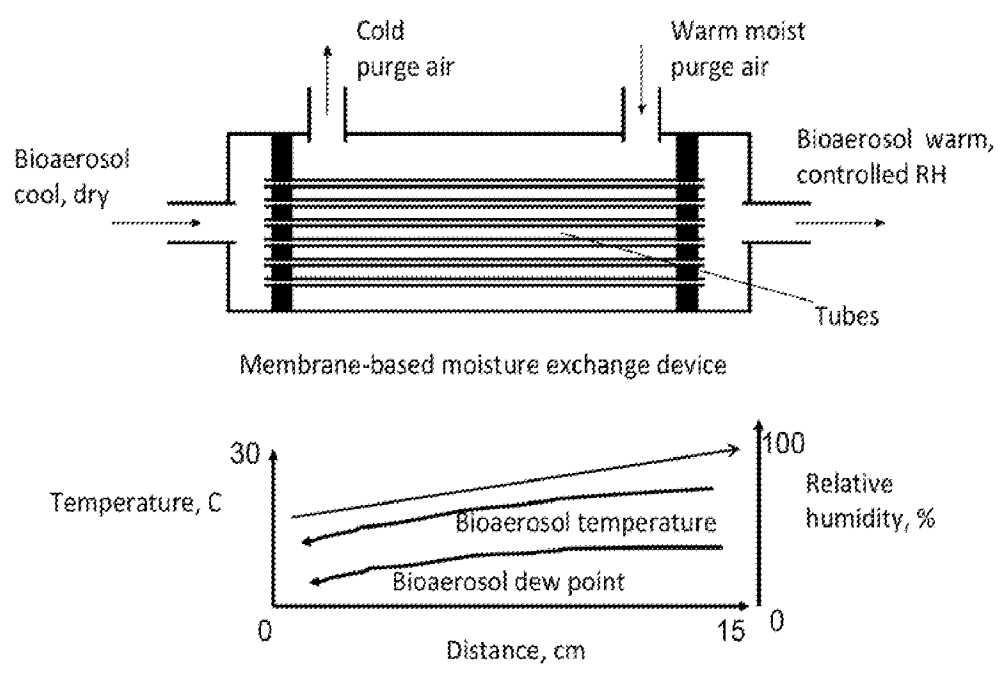

Control of the relative humidity and temperature at the point of sampling, where the temperature at the point of sampling is between 1° C. and ° 10 C, requires conditioning the sample air flow to along a pathway on the psychometric chart of FIG. 22 such that the sample flow remains subsaturated at all times, preferably in the relative humidity range between 40% and 90% RH. This combined temperature and relative humidity conditioning can be accomplished with the two-stage system illustrated in FIG. 24B (and FIG. 25C). Potentially the controlled process line on FIG. 23 could be realized because both the temperature and relative humidity would be changed in the membrane-based moisture exchange device of this invention. Examples of the potential membrane based devices are shown in FIGS. 28, 29, and 30. The gradients shown in FIGS. 28, 29, and 30 are merely representative of the temperature and humidity gradients used in the invention. As can be noticed, the maximum temperatures typically conform to outside ambient temperatures. As can be noticed, the predetermined temperatures typically conform to the targeted 4° C. type conditions. The same applies for the RH gradients. The length of the tubes in FIGS. 28, 29, and 30 over which the gradient exists is typically 15 cm, but distances as short as 1 to 2 cm and as long as 100 to 1000 cm (or possible greater) can be used. In these arrangements shown in FIGS. 28, 29 and 30, the properties of combined moisture and heat transfer are used to advantageously improve the viability of the collected microorganisms.

The driving force for moisture transfer is the difference in water vapor pressure between the bioaerosol in the tubes and the air introduced in the shell side of the device. The dew point is the temperature of moisture saturation. The relative humidity critical for bioaerosol viability is the ratio of mole fraction of water vapor of the bioaerosol divided by the mole fraction at saturation. Therefore, a path may be selected to maintain relative humidity with changing temperature and dew point temperature such as illustrated in FIG. 28.

Arrangements in FIGS. 29 and 30 might be used with advantage in a cascade as shown in FIG. 31. The vapor pressure of water (P) as a function of absolute temperature (T) in equilibrium with sorption sites in this device is given by (K. J. Leckrone and J. M. Myers, "Efficiency and temperature dependence of water removal by membrane dryers" Anal. Chem, 1997, 69(5), 911-918.)

$$\text{Log } P = -3580/T + 10.01$$

The implication is that the membrane-based moisture exchange device when applied as a dryer becomes much more effective as the temperature is reduced. Also the opposite is true, that elevated temperatures would facilitate humidification of the sample air. Further, heat transfer between the shell flow and tube flow would depend on the temperature difference across the membranes. However, the condensation of water is avoided by the control system of this invention to prevent loss of bioaerosol and reduction of efficiency of the moisture exchanger.

Factors which impact the collection and storage of viable microorganisms depends on a number of variables:
  Type of membrane in membrane-based moisture exchange device
  Diameter and wall thickness of the membrane tubes
  Number of membrane tubes
  Length of membrane tubes
  Plenum design in the moisture exchangers (The plenum design and the tube diameter will affect bioaerosol losses in the device.)
  Air flow rate of both the tube flow and shell flow. Normally the shell flow rate is at or above the tube flow rate.
  Temperature and relative humidity of the entering tube flow and entering shell flow.
  If a concurrent flow or counter current flow scheme is used between tube flow and shell flow.
In this invention, a series of moisture exchangers could be employed. Examples include the following:
  Cold dry sample—hot wet co-current shell flow to prevent drying, Hot dry sample—cold wet concurrent shell flow to prevent drying, Hot moist sample—cold dry countercurrent shell flow, and Cold moist sample—warm dry countercurrent shell flow.

The moisture exchange systems that can be used are manufactured by the Perma Pure, LLC corporation. An example is Model PH150-11060T-301 with 60 tubes and is about 40 cm long and 5 cm in diameter for conditioning bioaerosol flows of 25 liters per minute. The purge or jacket flow is maintained at 50 liters per minute.

In general, the controlled bioaerosol collection of this invention permits control of relative humidity during heating or cooling to preserve microorganisms by way of temperature gradients and/or RH gradients along a membrane-based moisture exchange system to control relative humidity during heating or cooling. The controlled bioaerosol collection of this invention permits the use of multiple cascaded membrane-based moisture exchange systems to control relative humidity during heating or cooling with different schemes for particular flows about the membrane elements.

In one embodiment of this invention, a membrane-based moisture exchange system creates a controlled relative humidity for bioaerosol sampling. Use of this moisture exchange system prevents cross contamination because the water is exchanged by a chemical process.

The control bioaerosol collection of this invention permits use of a sample by-pass in a bioaerosol sampling system. The sample by-pass is required to allow the system to reach desired temperature and relative humidity. When the appropriate bioaerosol conditions are reached at the bioaerosol collector, the sample flow can be switched from a by-pass mode to a sample collection mode to initiate obtaining a bioparticle sample.

Once the samples are collected, the temperature and RH humidity conditions are controlled as noted above to maintain the viability of the collected bioaresol organism. Further, the collection media can be relocated from the bioaerosol sampling system to a temperature and humidity controlled storage unit for transport or storage.

Experimental Evaluation

Three bioaerosol sampler prototypes following different embodiments of this invention have been used to evaluate particle collection, temperature and humidity conditioning, and maintenance of viability during sampling. For these tests, the viability is measured by comparison to a conventional all glass impinger (AGI) noted above. The three prototype samplers tested were:

(1) A "1-stage RH-conditioned biosampler" shown schematically in FIG. 24A, and implemented as shown in FIG. 25A. This system samples air at 25 L/min and is operated at ambient temperature and controls filter RH to approximately 80% at ambient temperature.

Figure 25B:
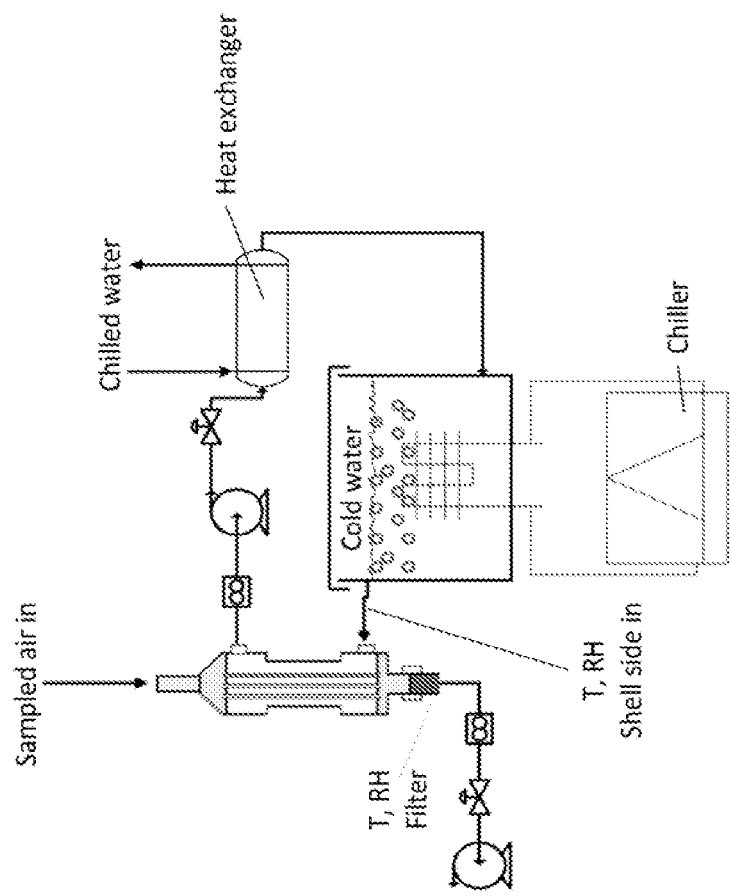
FIG. 25B is a depiction of another humidity control system of this invention.
Figure 25C:
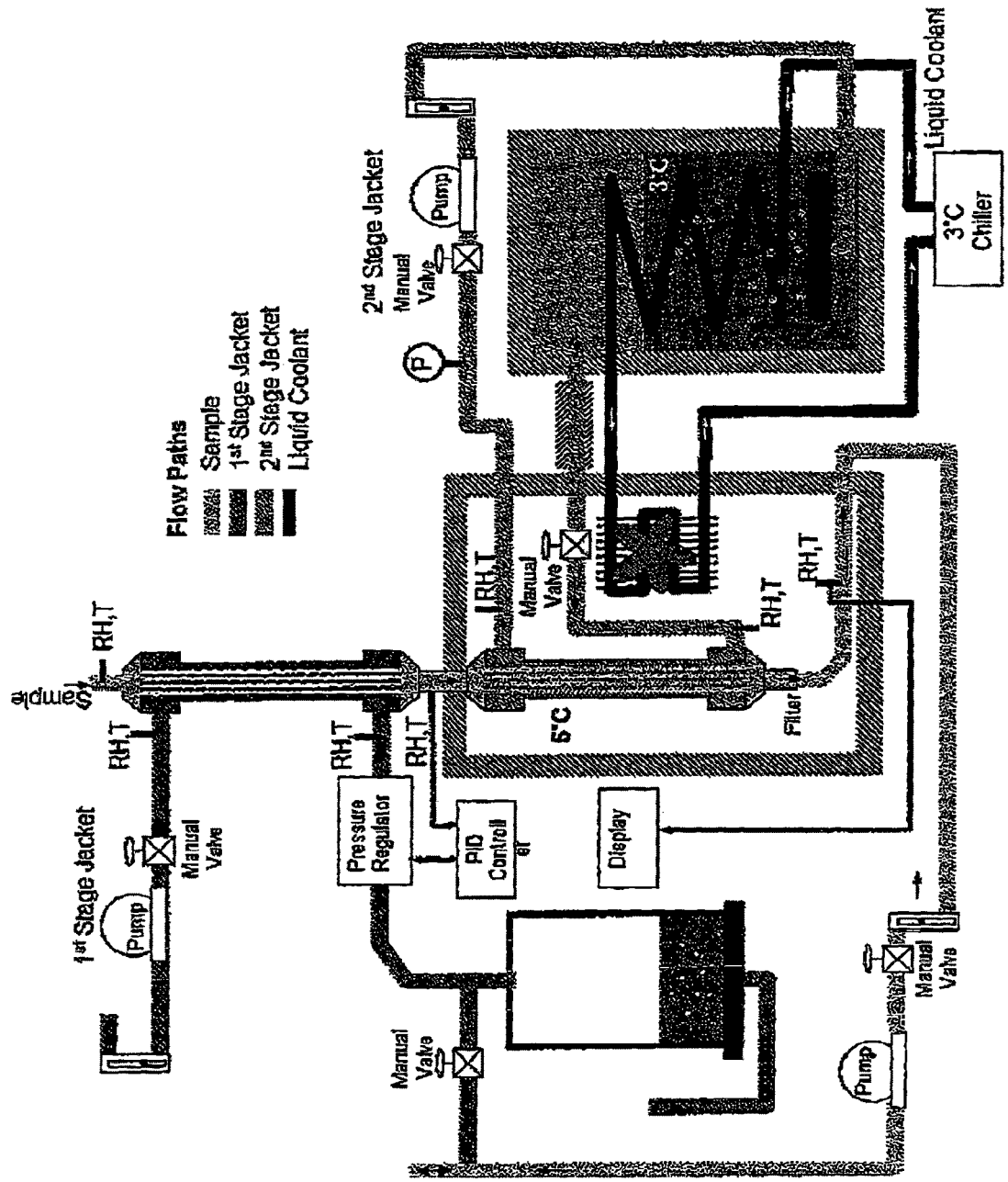
FIG. 25C is schematic diagram depicting a bioaerosol sampling system of this invention similar to the system shown in FIG. 24B with multiple or cascaded moisture devices.

(2) A "refrigerated 1-stage RH-conditioned biosampler" which is the second stage of the biosampler shown schematically in FIG. 24B, and implemented as shown in FIG. 25B. This system samples air at 25 L/min and cools the sampled air stream to approximately 11° C. and achieves at filter RH of approximately 75% using a Nafion unit and an air stream chilled by ice water.

(3) A "2-stage RH-conditioned biosampler" shown schematically in FIG. 24B, and implemented as shown in FIG. 25C. This is a 25 L/min system that uses a two-stage system of Nafion units to control the RH and temperature at the filter. Automated control of the first stage provides consistent RH at the inlet of the second stage that then cools the sample temperature to approximately 10° C. and provides an RH of approximately 80% at the filter.

Physical evaluation of the systems included measurement of particle penetration through the Nafion conditioner, and of the robustness of the relative humidity and temperature control. Biological or viability testing was done with four types of bioaerosols. These were *Bacillus thuringiensis* var. kurstaki (Btk), *E. coli*, MS2 phage, and *Yersinia*, where Btk is the hardiest, and Yesrinia the most fragile. A bioaerosol challenge of 10 minutes or 30 minutes was used followed by either no additional exposure or by sampling of clean air for several hours. As noted above, an all glass impinge (AGI) is used during the bioaerosol challenge time as a reference sample.

1-Stage Conditioning and Refrigerated 1-Stage RH-Conditioned Biosamplers

RH and Temperature Conditioning:

To test the performance of the conditioning system, the relative humidity at the point of the filter collector was measured over widely varying values of the relative humidity of the sampled air stream. FIG. 25D shows the results of these tests for the 1-stage conditioning biosampler. As the input relative humidity was decreased from around 90% to below 5%, the relative humidity measured at the sample filter remained almost constant close to 78%. This relative humidity control was achieved through an automated feedback system that adjusted the valve labeled "automated valve" in FIG. 25A to change the absolute pressure of the nearly-saturated flow in the shell space of the Nafion conditioner based on the value of the relative humidity at the sample filter as measured by the sensor labeled "RH sensor" in FIG. 25A.

Viability for Sampling:

Ability to maintain the viability of airborne organism during collection was evaluated using *E. coli*, wherein an AGI sampler served as reference. Consecutive, 30-min samples were collected with a pair of biosamplers and with the AGI operating in parallel. AGI samples were removed from the sampling line immediately, while one of the pair of samples from each biosampler was then subjected to another 16 to 24 hours of clean air sampling prior to being removed from the sampler. Comparison of viable collection for the runs with, and without multi-hour clean air exposure shows the viability of the *E. coli* during collection. Table 5 shows these results for several runs for the 1-stage RH-conditioned biosampler and the refrigerated 1-stage RH-conditioned biosampler, both referenced to the AGI. For a 30-minute challenge, significant recovery of *E. coli* is obtained for both biosamplers. For the 16-26 hr exposures following collection, the refrigerated sampler provided better recovery.

TABLE 5

*E. Coli* data comparing 1-stage RH-conditioned biosampler to the Refrigerated 1-Stage RH-conditioned BioSampler

| Test | Sampling time | 1-Stage RH-conditioned biosampler | | Refrigerated 1-Stage RH-conditioned biosampler | |
|---|---|---|---|---|---|
| | | CFU/L air | % of AGI | CFU/L air | % of AGI |
| Run 1 | 30 min | $1.0 \times 10^3$ | 103 | $1.0 \times 10^3$ | 118 |
| | 16.3 hr | $2.0 \times 10^{-2}$ | 0 | $2.0 \times 10^{-2}$ | 0.09 |
| Run 2 | 30 min | $1.2 \times 10^3$ | 76 | $1.2 \times 10^3$ | 54 |
| | 30 min | $1.5 \times 10^3$ | 77 | $1.5 \times 10^3$ | 91 |
| | 16 hr | $2.7 \times 10^{-2}$ | 0.001 | $2.7 \times 10^{-2}$ | 0.99 |

TABLE 5-continued

E. Coli data comparing 1-stage RH-conditioned biosampler to the Refrigerated 1-Stage RH-conditioned BioSampler

| Test | Sampling time | 1-Stage RH-conditioned biosampler | | Refrigerated 1-Stage RH-conditioned biosampler | |
|---|---|---|---|---|---|
| | | CFU/L air | % of AGI | CFU/L air | % of AGI |
| Run 3 | 30 min | $1.2 \times 10^3$ | 92 | $1.2 \times 10^3$ | 61 |
| | 30 min | $2.3 \times 10^3$ | 130 | $2.3 \times 10^3$ | 168 |
| | 16 hr | $3.3 \times 10^{-2}$ | 0.001 | $3.3 \times 10^{-2}$ | 3.8 |
| Run 4 | 30 min | | | $7.8 \times 10^2$ | 56 |
| | 24 hr | | | $3.5 \times 10^{-2}$ | 0.02 |
| Run 5 | 30 min | | | $8.9 \times 10^2$ | 38 |
| | 24 hr | | | $8.0 \times 10^{-2}$ | 0.003 |
| Run 6 | 30 min | | | $2.0 \times 10^3$ | 91 |
| | 24 hr | | | $4.7 \times 10^{-2}$ | 0.002 |

2-Stage Conditioning Biosampler

Figure 25E:
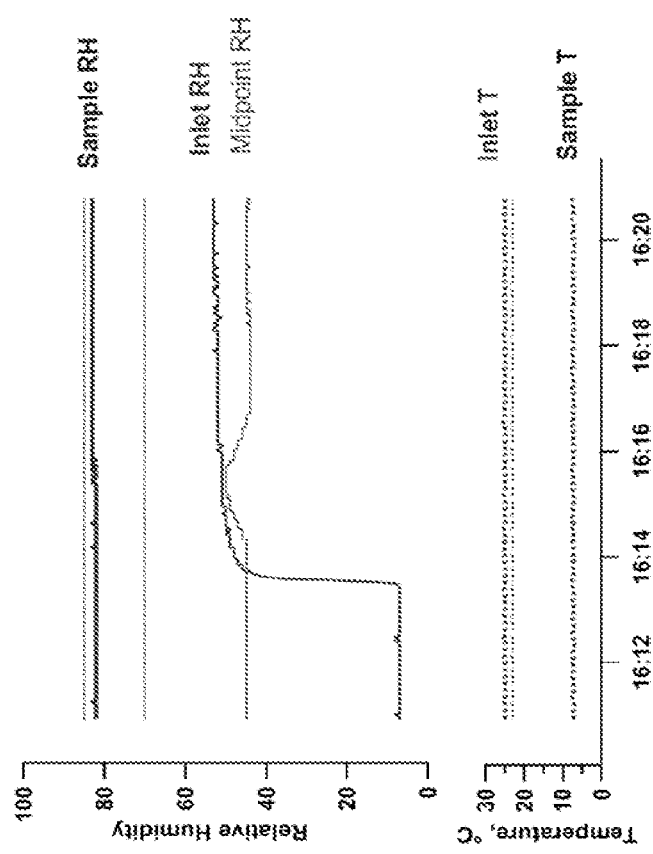
FIG. 25E is a schematic depicting two-stage humidity and temperature conditioning for a biosampler.

RH and Temperature Conditioning:

To test the performance of the 2-Stage conditioning biosampler, the temperature and relative humidity at the point of the filter collector was measured over widely varying values of the relative humidity of the sampled air stream. FIG. 25E show the temperature and humidity data attained in these laboratory tests. The first Nafion conditioning stage operated at ambient temperature. The shell pressure was controlled to bring the humidity of the exiting aerosol—the "Midpoint RH"—to a target of 45% RH. This conditioned flow entered the second Nafion conditioning stage, which had a cold shell flow at fixed humidity. The exiting sample humidity from this second stage is labeled "Sample RH." In FIG. 25E, the input relative humidity was rapidly changed from somewhat less than 10% to around 55%, and yet the relative humidity at the collection filter remained steady at around 82%.

Aerosol Penetration Tests:

Aerosol penetration through the 2-stage conditioning biosampler was tested using 2-µm fluorescent labeled polystyrene latex (PSL), with comparison to a sampling tube with 37-mm PTFE air sampling filter. The flow rates of 2-Stage Conditioning BioS ampler and the 37-mm reference sampling filter were both 25 L/min. Table 6 reports the results of three experiments with PSL aerosol. Overall, the recovery of PSL from the Nanofiber filters sampled with the 2-stage conditioning biosampler was lower than the recovery from Teflon filters sampled with the bare tube.

TABLE 6

Recovery of florescent 2 µm PSL aerosol for Nanofiber filers used in 2-stage conditioning biosampler compared to standard Teflon air sampling filter (reference filter).

| Experiment | Teflon Reference Filter (FSU) | 2-Stage Conditioning Biosampler-Nanofiber Filter (FSU) | NF % of Ref. |
|---|---|---|---|
| Run #1 | 4.8 | 4.0 | 82% |
| Run #2 | 10.5 | 4.5 | 43% |
| Run #3 | 11.4 | 9.7 | 85% |

Bioaerosol Contamination Testing:

Carryover or cross-contamination from one sample to the next was also investigated. Due to its hardiness, Bacillus thuringiensis var. kurstaki (Btk) was selected for this testing. Btk represents a design-limiting case where a hardy organism collects within the sampler and then could become re-entrained and deposited onto the collection filter during a later sampling time, thus contaminating the sampling filter. The test was conducted by challenging with Btk for 30 minutes followed by disconnecting 2-stage conditioning biosampler from the test rig, clearing the sampling line (about 1 minute of sampling the room air). A clean filter was installed, and sampling commenced for 30 minutes to collect potential re-entrained organisms. Table 7 summarizes the results for this experiment.

TABLE 7

Measurement of re-entrainment of Btk using 30 min challenge, filter change out, and 30 min of clean air. A minimal amount of organism was recovered indicating only minor carryover.

| Experiment | CFU/L air recovered | Reference to AGI |
|---|---|---|
| 30 min bioaerosol challenge | 94.3 | 117.6% |
| Clean filter + 30 clean air | 0.11 | N.A. |

Effect of Filter Quartering:

The effect of quartering filters (cutting into four quadrants) was studied with E. coli. A 10-minute challenge of aerosol was used with no exposure to clean air for the cases of whole filters versus quartered filters. The AGI was kept as a baseline for recovery of viable microbes. Table 8 summarizes the results. Table 8 presents the quartered filter data at recovery from whole filter processing, summation of all quarters of a single filter, and processing of each quarter. Interestingly, quartering the filter significantly deteriorates the viable recovery.

TABLE 8

Effect of quartering of filters using E coli as the test organism. Filters are challenged for 10 minutes with bioaerosol and then processed (no clean air exposure). Whole filters and quarter filters are compared by total organisms recovered relative to the AGI. Quartered filter data is presented as by individual piece and sum of the parts. Quartering filters significantly deteriorates recovery of microbes.

| Experiment | CFU/L air | Reference to AGI |
|---|---|---|
| Whole-#1 | 87 | 95% |
| Whole-#2 | 164 | 112% |
| Quartered-#3-Sum | 18 | 8% |
| #3-Q1 | 9.0 | 4.0% |
| #3-Q2 | 7.7 | 3.4% |
| #3-Q3 | 1.0 | 0.45% |
| #3-Q4 | 0 | 0.0% |
| Quartered-#4-Sum | 56 | 19% |
| #4-Q1 | 22 | 7.1% |
| #4-Q2 | 10 | 3.5% |
| #4-Q3 | 0.67 | 0.23% |
| #4-Q4 | 23 | 8.1% |

Viability for Sampling Btk.

Btk results for the 2-stage conditioning BioS ample are shown in Table 9. Recovery of viable Btk is accomplished in reasonable quantities. However, some loss relative to the AGI is observed. Previous experiments had shown that extraction of bacillus spores can be inefficient, likely due to interactions between the spore coat and the polymer nanofibers of the sampling filter. The longer aerosol challenge, 30 minutes, gave more favorable results. The longer challenge time provides more organisms loaded onto the sampler filter but does not change the relative amounts of bioaerosol collected by the 2-stage conditioning biosampler relative to the AGI.

TABLE 9

Results of Btk bioaerosol sampling by the 2-Stage Conditioning BioSampler prototype compared to the AGI reference. Recovery of Btk is achieved even with 4 hrs of clean air exposure but is, at most, approximately half that initially recovered by the AGI.

| Experiment | Organism Sample Time (minutes) | Clean air Sample Time (hours) | CFU/L air | Reference to AGI | Filter processing |
|---|---|---|---|---|---|
| Jul. 12, 2012 | 30 | 4 | 67 | 56% | whole |
| Jul. 23, 2012 | 10 | 4 | 5.3 | 26% | whole |
| Jul. 25, 2012 | 10 | 4 | 5.6 | 22% | whole |

Viability for Sampling *E. coli*.

Results for recovery of *E. coli* are summarized in Table 10. Several different experiments were conducted looking at the effect of challenge time, clean air exposure time, and filter quartering. Most results are single data points unless noted as an average. For a 30-minute challenge, significant recovery of *E. coli* is obtained indicating similar results to Btk for comparing 30-min and 10-min challenge times. A single 16-hr clean air challenge was conducted and the results, 0.5% viable recovery, compared well with previous results from the refrigerated RH-conditioned biosampler under the same conditions: 0.1% to 4% of the AGI for the Refrigerated RH-conditioned BioSampler. A 4-hr clean air challenge resulted in minimal loss of viability (compare 0 and 4-hr clean air challenges in Table 9).

TABLE 10

Results of *E. coli* bioaerosol sampling for various experimental conditions. Viable recovery is best for a whole filter and 4 hrs of clean air challenge.

| Experiment | Organism Sample Time (minutes) | Clean air Sample Time (hours) | CFU/L air | Reference to AGI | Filter type |
|---|---|---|---|---|---|
| 30 min whole | 30 | 0 | 1567 | 153% | Whole |
| 30 min whole + air | 30 | 16 | 5.4 | 0.49% | Whole |
| 10 min whole | 10 | 0 | 126 | 103% | Whole (average two samples) |
| 10 min whole + air | 10 | 4 | 286 | 146% | Whole |

Control of the Bioaerosol Collection System

Figure 32:
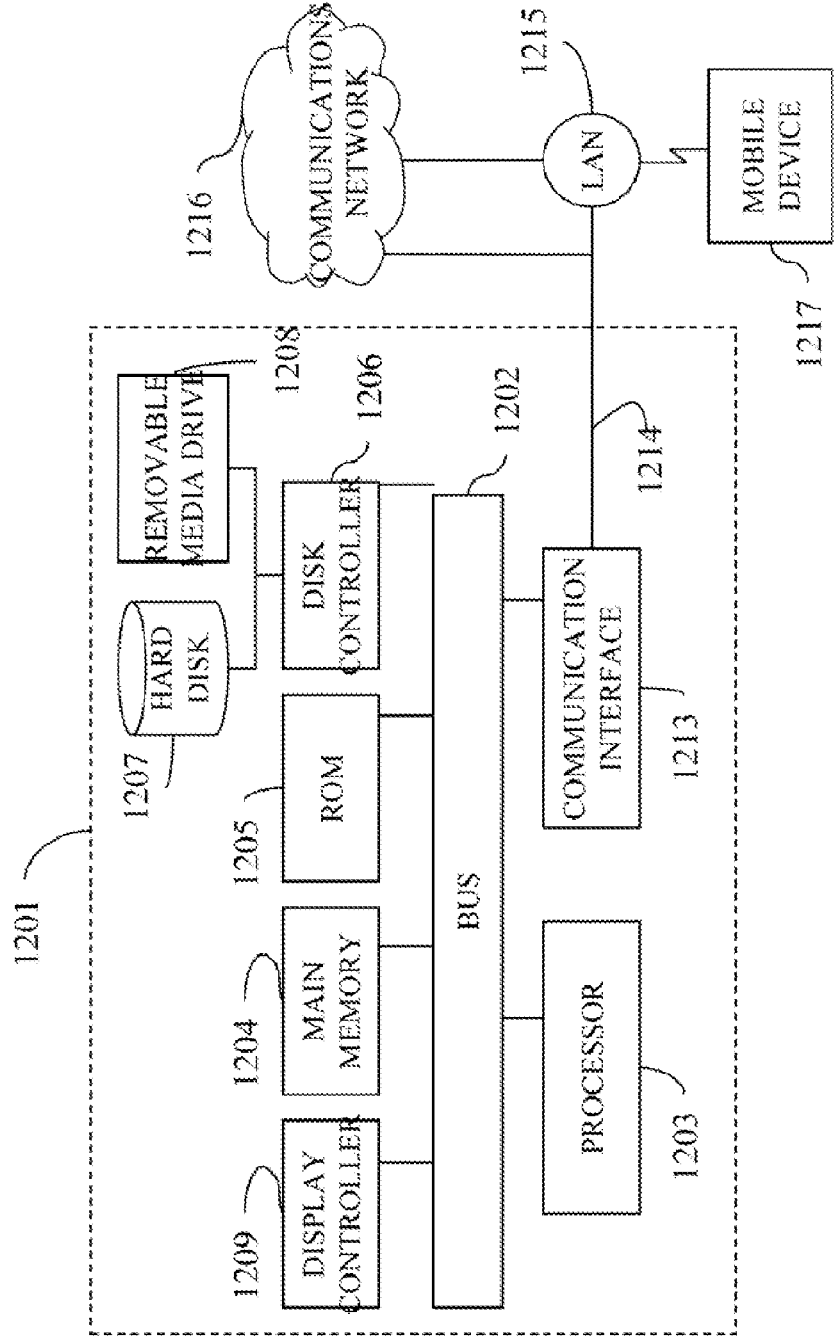
FIG. 32 is a schematic illustration of a computer system for implementing various embodiments of this invention including control of the bioaresol collection.

Control of the bioaerosol collection system of this invention is typically under processor control. FIG. 32 illustrates a computer system 1201 for implementing various embodiments of this invention. The computer system 1201 may be used as the computer system 5 to perform any or all of the control functions described above to regulate gas flow, temperature and humidity. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210.

The computer system 1201 performs a portion or all of the control functions described above by having instructions programmed to perform various steps for control of the humidifier, air stream, refrigeration, RH, and temperature gradients. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Generalized Aspects of the Invention

In one aspect of the invention, an aerosol collection system includes a bio-aerosol delivery device configured to supply bioparticles in a gas stream, a moisture exchange device including a partition member coupled to the gas stream and configured to humidify or dehumidify the bioparticles in the gas stream with a vapor of a biocompatible liquid (e.g., water or other non-toxic fluid), and an aerosol collection medium downstream from the moisture exchange device and configured to collect the bioparticles.

In this aspect, the moisture exchange device can be at least one of a permeable material, a semi-permeable membrane material, or a polymeric ionomer. The moisture exchange device include least one of:
- a copolymer of perfluoro-3,6-dioxa-4-methyl-7octene-sulfonic acid and tetrafluoroethylene;
- polyethylene oxide, polyvinyl alcohol, cellulose ether and starch) and copolymers thereof; and
- polyacrylic acid, polyacrylamide, polyisopropyl acrylamide, polystyrene sulfonic acid, polyvinyl pyridine and polyamino acid and copolymers and salts thereof.

The moisture exchange device include tubes of at least one of a permeable material, a semi-permeable membrane material, or a polymeric ionomer. The moisture exchange device include tubes of at least one of:
- a copolymer of perfluoro-3,6-dioxa-4-methyl-7octene-sulfonic acid and tetrafluoroethylene;
- polyethylene oxide, polyvinyl alcohol, cellulose ether and starch, and copolymers thereof; and
- polyacrylic acid, polyacrylamide, polyisopropyl acrylamide, polystyrene sulfonic acid, polyvinyl pyridine and polyamino acid and copolymers and salts thereof.

In this aspect, the aerosol collection system can include a by-pass gas flow device configured to supply air flow without the entrained bioparticles in order stabilize at least one of a temperature and relative humidity of the aerosol collection medium prior to collecting the bioparticles.

In this aspect, the aerosol collection system can include a controller configured to control temperature and a relative humidity along a gas-flow axis of the membrane-based moisture exchange device. The controller can be programmed to adjust the temperature and the relative humidity such that the particles in the gas stream transition from outside ambient conditions to a target temperature and relative humidity condition. The target temperature and relative humidity condition can be controlled to be in at least one of the following conditions:
- 4° C., and RH of 5 to 95%;
- 2° C. to 6° C., and RH of 5 to 95%;
- 1° C. to 8° C., and RH of 5 to 95%; or
- 2° C. to 10° C., and RH of 5 to 95%.

The controller can be programmed to adjust a temperature and a relative humidity of the bioparticle while transitioning from outside ambient conditions to the target temperature and relative humidity condition along a controlled path of temperature and humidity. The controlled path maintains a relative humidity level greater than 5%, greater than 10%, greater than 15%, greater than 25%, or greater than 50%, during transport of the bioparticles to the collection medium.

With the conditioned biosamplers of this invention, the target temperature and relative humidity condition can be controlled to be in at least one of the following conditions:
- 1° C. to 10° C., and RH of 50 to 95%;
- 1° C. to 10° C., and RH of 60 to 90%; or preferably
- 1° C. to 10° C., and RH of 70 to 85%; or more preferably
- 2° C. to 12° C., and RH of 70 to 85%.

Alternatively, if sampling in an indoor environment, with retrieval of the sample shortly after collection, then it is possible to control the humidity condition of the sampling. In this instance, active temperature control may not be needed, and instead the humidity only is controlled. The relative humidity condition can be controlled to be in one of the following conditions:
- RH of 50% to 95%;
- RH of 60% to 90%; or preferable
- RH of 70% to 85%; or more preferably
- RH of 75% to 85%.

In this aspect, the aerosol collection medium can be at least one of a flow-through or an impaction device including a plurality of fibers.

In this aspect, the aerosol collection medium can include a viability enhancing material provider disposed in a vicinity of the plurality of fibers and configured to provide a viability enhancing material to the collected bioparticles to maintain viability of the collected bioparticles. The viability enhancing material provider can include an osmotic material disposed in contact with the plurality of fibers and configured to maintain a relative humidity suitable for said viability of bioparticles. The osmotic material can be a water-regulating material configured to provide water and/or a nutrient supply to the fibers to support biological viability of the collected bioparticles. The nutrient supply can include a supply of at least one of water, proteins, carbohydrates, sugars, salts, phosphate buffered saline, and tryptic soy broth.

In this aspect, the aerosol collection medium can be a plurality of fibers formed into a fiber mat for collection of the bioaerosol particles. The plurality of fibers can have an average fiber diameter of less than 10 microns. The plurality of fibers can have an average fiber diameter of less than 1 micron. The plurality of fibers can have an average fiber diameter of less than 0.5 micron.

In this aspect, the biocompatible liquid can include solutions including at least one or more of water, proteins, carbohydrates, sugars, salts, phosphate buffered saline, and tryptic soy broth.

In another aspect of the invention, a method for collecting aerosols includes delivering bioparticles in an gas stream, humidifying or dehumidifying the bioparticles in the gas stream by transport of water or other non-toxic fluid across a partition member and into a vapor phase of the gas stream, and collecting the bioparticles by a collection medium.

The humidifying or dehumidifying can maintain a relative humidity greater than 5%, greater than 10%, greater than 15%, greater than 25%, or greater than 50%. The humidifying or dehumidifying can transport the biocompatible liquid across at least one of a permeable material, a semi-permeable membrane material, or a polymeric ionomer. The humidifying or dehumidifying can transport the biocompatible liquid across at least one of:
- a copolymer of perfluoro-3,6-dioxa-4-methyl-7octene-sulfonic acid and tetrafluoroethylene;
- polyethylene oxide, polyvinyl alcohol, cellulose ether and starch, and copolymers thereof; and
- polyacrylic acid, polyacrylamide, polyisopropyl acrylamide, polystyrene sulfonic acid, polyvinyl pyridine and polyamino acid and copolymers and salts thereof.

In this aspect, the method for collecting aerosols can stabilize the temperature and/or the relative humidity of the aerosol collection medium prior to collecting the bioparticles. In this aspect, the method for collecting aerosols can control a temperature and a relative humidity along a gas-flow axis of the membrane.

In this aspect, the method for collecting aerosols can adjust the temperature and the relative humidity such that the particles in the gas stream transitions from outside ambient conditions to a target temperature and relative humidity condition. In this aspect, the method for collecting aerosols can adjust the temperature and the relative humidity to at least one of the following conditions:
- 4° C., and RH of 5 to 95%;
- 2° C. to 6° C., and RH of 5 to 95%;
- 1° C. to 8° C., and RH of 5 to 95%; or
- 2° C. to 10° C., and RH of 5 to 95%.

Other conditions for collecting aerosols include the adjusting of the relative humidity at the point of sampling to range between 50% and 90% and more preferably between 75% to 85% range both at ambient collection temperature (e.g., ~20-25° C.) and at cooled temperatures (e.g., 4-10° C.).

Accordingly, in one embodiment, the present invention provides for viable collection of bioaerosol through control of the relative humidity at the point of sampling to the range of 75% to 85%. Collection at this target relative humidity range can provide viable sampling at ambient temperatures, or at refrigerator temperatures, where refrigerator temperatures are defined as in the range between 1° C. and 10° C. When there is a need to store the sample for an extended time, sampling can occur at refrigerator temperatures.

The embedded results below show the percentage recovery of viral simulants as compared to collection of these simulants under "normal" room temperature and humidity conditions were these simulants normally doe not survive and are not recoverable. Collecting at the higher humidity conditions improves the recoverability.

| Conditions | | % Recovered | |
|---|---|---|---|
| RH | T (C.) | Yersinia r. | Serratia |
| 40% | 22 | 0% | 0% |
| 80% | 22 | 0% | 11% |
| 80% | 10 | 0.2% to 20% | not tested |

| | | Organism % Recovered | | | | |
|---|---|---|---|---|---|---|
| RH | T | Bacillus | E coli | Serratia | Yersinia | MS2 |
| 80% | 22° C. | 30 ± 17% | N.T. | 11% | 0% | N.T. |
| 80% | 10° C. | 79 ± 5% | 40 ± 20% | N.T. | 0.2 to 20% | 11 ± 7% |

N.T. = not tested

In this aspect, the method for collecting aerosols can adjust a temperature and a relative humidity of the bioparticle while transitioning from outside ambient conditions to the target temperature and relative humidity condition along a controlled path of temperature and humidity, where the controlled path maintains a relative humidity level greater than 5%, greater than 10%, greater than 15%, greater than 25%, or greater than 50%, during transport of the bioparticles to the collection medium.

In this aspect, the method for collecting aerosols can provide a viability enhancing material to the collection medium such as for example water, proteins, carbohydrates, sugars, salts, phosphate buffered saline, and/or tryptic soy broth.

In this aspect, the method for collecting aerosols can collect at least one of pox viruses, filoviruses, arenaviruses, alphavirus, *brucella* species, *burkholderia mallei*, *Yersinia pestis* and *Coxiella burnetii* on the collection medium.

In another aspect of the invention, a collection device includes a plurality of fibers formed into a fiber mat. The fiber mat is configured to collect and maintain the viability of microbes and/or bioparticles. The fibrous filter can be configured in any manner used in air sampling/aerosol collection using a flow-through filter. In one aspect of the invention, the fibers are configured as an impaction substrate to collect and maintain microbes and/or bioparticles for use in air sampling/aerosol collection using the method of impaction. The fibrous filter can be configured in any manner used for swabbing or the wiping of surfaces or the sampling of bioparticles in liquids.

In another aspect of the invention, there is provided a bioparticle collection device including a collection medium including a plurality of fibers formed into a fiber mat and configured to collect bioparticles thereon, and including a viability enhancing material provider disposed in a vicinity of the plurality of fibers and configured to provide a viability enhancing material to the collected bioparticles to maintain viability of the bioparticles collected by the fiber mat. In this aspect of the invention, the viability enhancing material may or may not be a subset of the plurality of fibers.

In one aspect of the invention, the filter or impaction substrate includes a fibrous mat configured in terms of structure, surface chemistry, and additives to provide enhanced support of viability maintenance of the bioparticles collected.

In one aspect of the invention, a filtration or impaction device for aerosol collection includes a fibrous mat and in conjunction with a mechanism or method for conditioning the moisture content of the air entering the air sampling device to a value that provides enhanced collection and maintenance of the bioparticles collected.

In one aspect of the invention, the air flow containing bioaerosol is conditioned as to relative humidity and temperature, and the particles therein are collected by impaction onto a fibrous substrate or by a subsequent filtration mechanism. The fibrous substrate and/or the subsequent filtration mechanism provide a collection mechanism of bioparticles and provide a mechanism for maintenance of viability of the collected bioparticles.

In one aspect of the invention, the aerosol is exposed to the vapor or a working fluid (such as for example water and other fluids that are biocompatible, possibly including silicone fluids) in a saturation chamber. Subsequently, vapor condensation onto particles is induced by either adiabatic expansion or cooling in the condensing chamber, or by mixing with a cooler airflow. The enlarged particles are subsequently collected via impaction or filtration on a nanofiber or fiber material.

In one aspect of the invention, a fibrous mat is configured to provide enhanced recovery of the collected material. Enhanced recovery includes 1) recovery of the particles such that the extraction procedure does not decrease their viability; 2) a collection and extraction which does not prevent or impede subsequent analysis such as live culture, PCR-based techniques, or any other chemical or physical analysis of the collected material/organisms; and 3) enhanced release of the collected material through dissolution of the fibrous material using select solvents and/or processing conditions.

In one aspect of the invention, the fibers in the fibrous material or the fiber mat have an average fiber diameter of less than 10 Φm, or less than 1 Φm, or less than 500 nm, or less than 300 nm, or less than 200 nm, or less than 100 nm.

In another aspect of the invention, there is provided a method for collecting aerosols. This method includes entraining particles in a gas stream, exposing the particles in the gas stream to a solvent, and collecting the aerosol particles by a collection medium. The collection medium includes a plurality of fibers formed into a fiber mat including and a viability enhancing material provider disposed in a vicinity of the plurality of fibers and configured to provide a viability enhancing material to the collected bioparticles to maintain viability of the bioparticles collected by the fiber mat.

This method also can inject the viability enhancing material into the collection medium prior to collecting the aerosol particles. The viability enhancing material injected can be at least one of water, proteins, carbohydrates, sugars, salts, phosphate buffered saline, and tryptic soy broth. This method also can inject the viability enhancing material (such as those listed above) into the collection medium during the collecting of the aerosol particles. This method also can inject antioxidants such as for example nitrous oxide (NO) into the collection medium.

This method also can introduce an agent to reduce oxygen toxicity to the bioparticles collected in the collection medium. Such an agent can include enzymes or fullerenes to reduce oxygen toxicity.

In another aspect of the invention, there is provided a bioparticle collection device including a collection medium including a plurality of fibers formed into a fiber mat and an osmotic material disposed in contact with the plurality of fibers. The osmotic material can be a viability enhancing material configured to maintain viability of bioparticles collected by the fiber mat. The osmotic material can be a water-regulating material configured to provide water to the fibers. The osmotic material can constitute a nutrient supply providing nutrients to support biological viability of biomaterial collected in the filtration medium. The nutrient supply can be at least one of water, proteins, sugars, carbohydrates, salts, phosphate buffered saline, and tryptic soy broth.

The collection medium and the viability enhancing material can be disposed in one of an air filter, a wipe, a brush, a swab, a sorbent pad, or a liquid filter. The fibers can be made of materials which are dissolvable in a bio-compatible solvent.

The collection medium can include a support (e.g., a rigid support) supporting the collection medium. The support can be one of a filter, a plastic foam, a metallic foam, a semi-conductive foam, a woven material, a nonwoven material, a plastic screen, a textile, and a high efficiency particulate air (HEPA) filter medium.

In another aspect of the invention, there is provided an aerosol collection system including an aerosol pumping device configured to entrain particles in a gas stream, an aerosol saturation device configured to expose the particles in the gas stream with a biocompatible liquid, and an aerosol collection medium downstream from the aerosol saturation device. The aerosol collection medium includes a plurality of fibers formed into a fiber mat for collection of the aerosol particles, and an osmotic material disposed in contact with the plurality of fibers.

The aerosol collection system can include a humidity control device configured to maintain the collection medium at a relative humidity from 50 to 100%, or at a relative humidity from 65 to 85%, or at a relative humidity from 75 to 81%.

The aerosol collection medium in this aspect of the invention can be at least one of a flow-through or an impaction device. The osmotic material in this aspect of the invention can be a viability enhancing material configured to maintain viability of bioparticles collected by the fiber mat. The osmotic material in this aspect of the invention can be a water-regulating material configured to provide water to the fibers. The osmotic material in this aspect of the invention can be a nutrient supply providing nutrients to support biological viability of biomaterial collected in the filtration medium. The nutrient supply in this aspect of the invention can be a supply of at least one of proteins, sugars, and salts.

The fibers in this aspect of the invention can be nanofibers, can be formed of materials dissolvable in a bio-compatible solvent. A support (rigid or not) can be used to support the collection medium. The support in this aspect of the invention can be at least one of a filter, a plastic foam, a metallic foam, a semi-conductive foam, a woven material, a nonwoven material, a plastic screen, a textile, and a high efficiency particulate air (HEPA) filter medium.

In another aspect of the invention, there is provided a method for collecting aerosols. The method included entraining particles in an gas stream, exposing the particles in the gas stream to a biocompatible liquid, and collecting the aerosol particles by a collection medium including a plurality of fibers formed into a fiber mat including and an osmotic material disposed in contact with the plurality of fibers.

This method also can inject the viability enhancing material into the collection medium prior to collecting the aerosol particles. The viability enhancing material injected can be at least one of water, proteins, carbohydrates, sugars, salts, phosphate buffered saline, and tryptic soy broth. This method also can inject the viability enhancing material (such as those listed above) into the collection medium during the collecting of the aerosol particles. This method also can inject antioxidants such as for example nitrous oxide (NO) into the collection medium.

This method also can introduce an agent to reduce oxygen toxicity to the bioparticles collected in the collection medium. Such an agent can include enzymes or fullerenes to reduce oxygen toxicity.

In another aspect of the invention, there is provided a bioparticle collection device including a collection medium including a plurality of fibers formed into a fiber mat and an osmotic material disposed in contact with the plurality of fibers. The osmotic material can be a viability enhancing material configured to maintain viability of bioparticles collected by the fiber mat. The osmotic material can be a water-regulating material configured to provide water to the fibers. The osmotic material can constitute a nutrient supply providing nutrients to support biological viability of biomaterial collected in the filtration medium. The nutrient supply can be at least one of water, proteins, sugars, carbohydrates, salts, phosphate buffered saline, and tryptic soy broth.

The collection medium and the viability enhancing material can be disposed in one of an air filter, a wipe, a brush, a swab, a sorbent pad, or a liquid filter. The fibers can be made of materials which are dissolvable in a bio-compatible solvent.

The bioparticle collection device can include a support (e.g., a rigid support) supporting the collection medium. The support can be one of a filter, a plastic foam, a metallic foam, a semi-conductive foam, a woven material, a nonwoven material, a plastic screen, a textile, and a high efficiency particulate air (HEPA) filter medium.

Numerous modifications and variations of the invention are possible in light of the above teachings. It is therefore to be understood that within the scope of the appended claims, the invention may be practiced otherwise than as specifically described herein.

The invention claimed is:
1. An aerosol collection system comprising:
a moisture exchange device comprising at least one partition member separating a first gas stream and a second gas stream, wherein bioparticles in the second gas stream exist in a controlled relative humidity environment by transport of water vapor a) from an exterior side of the at least one partition member to an interior side of the at least one partition member and b) into a vapor phase of the second gas stream including the bioparticles;

a bio-aerosol delivery device configured to supply bioparticles into the second gas stream;

a pressure control device configured to control a pressure in the first gas stream and thereby control the transport of water vapor through the at least one partition member; and an aerosol collection medium downstream from the moisture exchange device and configured to collect the bioparticles.

2. The system of claim 1, wherein the at least one partition member comprises at least one of a permeable material, a semi-permeable membrane material, or a polymeric ionomer.

3. The system of claim 1, wherein the at least one partition member comprises at least one of:

a copolymer of perfluoro-3,6-dioxa-4-methyl-7octene-sulfonic acid and tetrafluoroethylene;

polyethylene oxide, polyvinyl alcohol, cellulose ether and starch) and copolymers thereof; and polyacrylic acid, polyacrylamide, polyisopropyl acrylamide, polystyrene sulfonic acid, polyvinyl pyridine and polyamino acid and copolymers and salts thereof.

4. The system of claim 1, wherein the at least one partition member comprises at least one tube of at least one of a permeable material, a semi-permeable membrane material, or a polymeric ionomer.

5. The system of claim 1, wherein the at least one partition member comprises at least one tube of at least one of:

a copolymer of perfluoro-3,6-dioxa-4-methyl-7octene-sulfonic acid and tetrafluoroethylene;

polyethylene oxide, polyvinyl alcohol, cellulose ether and starch) and copolymers thereof; and polyacrylic acid, polyacrylamide, polyisopropyl acrylamide, polystyrene sulfonic acid, polyvinyl pyridine and polyamino acid and copolymers and salts thereof.

6. The system of claim 1, further comprising:

a by-pass gas flow device configured to supply air flow without the entrained bioparticles into the second gas stream in order stabilize at least one of a temperature and relative humidity in the moisture exchange device prior to collecting the bioparticles.

7. The system of claim 1, further comprising:

a controller configured to control a temperature and a relative humidity along a gas-flow axis of the moisture exchange device.

8. The system of claim 7, wherein the controller is programmed to adjust the temperature and the relative humidity such that the particles in the second gas stream transition from outside ambient conditions to a target temperature and relative humidity condition.

9. The system of claim 8, wherein the target temperature and relative humidity condition comprises at least one of:

2° C. to 10° C. and RH of 5 to 95%

2° C. to 10° C. and RH of 70 to 85%;

1° C. to 8° C. and RH of 5 to 95%;

1° C. to 8° C. and RH of 70 to 85%;

2° C. to 6° C. and RH of 5 to 95%;

2° C. to 6° C. and RH of 70 to 85%;

4° C. and RH of 5 to 95%; or

4° C. and RH of 70 to 85%, where RH is the relative humidity in the second gas stream.

10. The system of claim 8, wherein the controller is programmed to adjust the temperature and the relative humidity in the second gas stream while transitioning from outside ambient conditions to the target temperature and relative humidity condition along a controlled path of temperature and humidity, said controlled path comprises a two-stage system including a first stage having the relative humidity in a range from 40-60% at ambient temperature and a second stage below ambient temperature while maintaining the relative humidity in said range from 40-60%.

11. The system of claim 1, wherein the aerosol collection medium comprises at least one of a flow-through or an impaction device including a plurality of fibers.

12. The system of claim 11, wherein the aerosol collection medium comprises a viability enhancing material provider disposed in a vicinity of the plurality of fibers and configured to provide a viability enhancing material to the collected bioparticles to maintain viability of the collected bioparticles.

13. The system of claim 12, wherein the viability enhancing material provider comprises an osmotic material disposed in contact with the plurality of fibers and configured to maintain a relative humidity suitable for said viability of bioparticles.

14. The system of claim 13, wherein the osmotic material comprises at least one of a water-regulating material configured to provide water or a nutrient supply to the fibers to support biological viability of the collected bioparticles.

15. The system of claim 14, wherein the nutrient supply comprises a supply of at least one of water, proteins, carbohydrates, sugars, salts, phosphate buffered saline, and tryptic soy broth.

16. The system of claim 1, wherein the aerosol collection medium comprises a plurality of fibers formed into a fiber mat for collection of the bioaerosol particles.

17. The system of claim 16, wherein the fibers have an average fiber diameter of less than 10 microns.

18. The system of claim 16, wherein the fibers have an average fiber diameter of less than 1 micron.

19. The system of claim 16, wherein the fibers have an average fiber diameter of less than 0.5 micron.

20. The system of claim 1, wherein the at least one partition member comprises multiple tubes having respective walls separating the first gas stream and the second gas stream.

* * * * *